US012714754B2

(12) United States Patent
Cabral et al.

(10) Patent No.: US 12,714,754 B2
(45) Date of Patent: Aug. 25, 2026

(54) DELIVERY OF CYCLIC COMPOUND BY USING CARRIER

(71) Applicant: THE UNIVERSITY OF TOKYO, Tokyo (JP)

(72) Inventors: Horacio Cabral, Tokyo (JP); Takuya Miyazaki, Tokyo (JP); George Huang, Tokyo (JP); Anqi Tao, Tokyo (JP); Yoshihiro Tachihara, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 1421 days.

(21) Appl. No.: 17/299,960

(22) PCT Filed: Dec. 6, 2019

(86) PCT No.: PCT/JP2019/047900
§ 371 (c)(1),
(2) Date: Aug. 27, 2021

(87) PCT Pub. No.: WO2020/116635
PCT Pub. Date: Jun. 11, 2020

(65) Prior Publication Data

US 2021/0386869 A1 Dec. 16, 2021

(30) Foreign Application Priority Data

Dec. 7, 2018 (JP) ................................ 2018-229598

(51) Int. Cl.

| | |
|---|---|
| ***A61K 9/16*** | (2006.01) |
| ***A61K 9/50*** | (2006.01) |
| ***A61K 31/7048*** | (2006.01) |
| ***A61K 38/12*** | (2006.01) |
| ***A61K 38/15*** | (2006.01) |
| ***A61K 47/54*** | (2017.01) |
| ***A61K 47/69*** | (2017.01) |

(52) U.S. Cl.
CPC ........ *A61K 47/6949* (2017.08); *A61K 9/1629* (2013.01); *A61K 31/7048* (2013.01); *A61K 38/12* (2013.01); *A61K 38/15* (2013.01); *A61K 47/545* (2017.08)

(58) Field of Classification Search
CPC .............. A61K 47/6949; A61K 9/1629; A61K 31/7048; A61K 38/12; A61K 38/15; A61K 47/545; A61K 47/595; A61K 47/60; A61K 47/6907; A61P 35/00
See application file for complete search history.

(56) References Cited

U.S. PATENT DOCUMENTS

| | | | |
|---|---|---|---|
| 7,829,657 | B2 | 11/2010 | Kataoka et al. |
| 8,853,167 | B2 | 10/2014 | Kato et al. |
| 8,895,076 | B2 | 11/2014 | Kataoka et al. |
| 9,821,024 | B2 | 11/2017 | Aversa et al. |
| 9,937,263 | B2 | 4/2018 | Kataoka et al. |
| 10,912,838 | B2 | 2/2021 | Kataoka et al. |
| 2008/0249049 | A1 | 10/2008 | Kataoka et al. |
| 2009/0018216 | A1 | 1/2009 | Kataoka et al. |
| 2009/0258416 | A1 | 10/2009 | Kataoka et al. |
| 2010/0221320 | A1 | 9/2010 | Kataoka et al. |
| 2011/0110881 | A1 | 5/2011 | Kataoka et al. |
| 2012/0053295 | A1 | 3/2012 | Kataoka et al. |
| 2012/0149649 | A1 | 6/2012 | Kato et al. |
| 2013/0243873 | A1 | 9/2013 | Aversa et al. |
| 2014/0017328 | A1 | 1/2014 | Kataoka et al. |
| 2016/0051484 | A1 | 2/2016 | Kataoka et al. |
| 2016/0287714 | A1 | 10/2016 | Kataoka et al. |
| 2018/0008549 | A1 | 1/2018 | Kataoka et al. |
| 2018/0008550 | A1 | 1/2018 | Kataoka et al. |
| 2018/0042989 | A1 | 2/2018 | Aversa et al. |
| 2018/0185501 | A1 | 7/2018 | Kataoka et al. |
| 2020/0197527 | A1 | 6/2020 | Kataoka et al. |
| 2021/0187005 | A1 | 6/2021 | Kataoka et al. |

FOREIGN PATENT DOCUMENTS

| | | | |
|---|---|---|---|
| CN | 106943603 | A | 7/2017 |
| JP | 2013543880 | A | 12/2013 |
| WO | 2006085664 | A1 | 8/2006 |
| WO | 2007099660 | A1 | 9/2007 |
| WO | 2007099661 | A1 | 9/2007 |
| WO | 2009157279 | A1 | 12/2009 |
| WO | 2010093036 | A1 | 8/2010 |
| WO | 2011105402 | A1 | 9/2011 |
| WO | 2012096399 | A1 | 7/2012 |
| WO | 2014133172 | A1 | 9/2014 |
| WO | 2015075942 | A1 | 5/2015 |
| WO | 2015170757 | A1 | 11/2015 |

OTHER PUBLICATIONS

Harada et al. (Acc. Chem. Res. 2014, 47, 2128-2140).*
Sugawara et al. (Langmuir 1992, 8, 609-612).*
Guo et al. (Macromolecules 2008, 41, 8677-8681).*
Zhang et al. (Angew. Chem. 2009, 121,982-986).*
Ponta et al. (Pharm. Res. 2010 27:2330-2342).*
Jia et al. (Macromolecules 2018, 51, 8455-8460).*
Ulfkjær et al. (Nanoscale 2018, 10, 9133-9140).*
Chen et al. (J. Am. Chem. Soc. 2018, 140, 17992-17998).*
English translation of International Search Report for parent application No. PCT/JP2019/047900 dated Mar. 3, 2020.

(Continued)

*Primary Examiner* — Michael G. Hartley
*Assistant Examiner* — Melissa J Perreira
(74) *Attorney, Agent, or Firm* — J-TEK LAW PLLC; Jeffrey D. Tekanic; Scott T. Wakeman

(57) ABSTRACT

A drug delivery system delivers a cyclic compound to a target cell or tissue while suppressing the pharmacological activity of the cyclic compound. A complex includes the cyclic compound and a delivery carrier having a shaft portion for carrying the cyclic compound. The shaft portion is complexed by inclusion in the cyclic compound to form a host-guest complex.

8 Claims, 26 Drawing Sheets

(56) References Cited

OTHER PUBLICATIONS

English Translation of the Written Opinion of the International Searching Authority for parent application No. PCT/JP2019/047900 dated Mar. 3, 2020.
F. Albericio, et al. "Therapeutic Peptides", Future Med. Chem., (2012) 4(12), pp. 1527-1531.
S. Zeng, et al., "Trilayer micelles for combination delivery of rapamycin and siRNA targeting Y-box binding protein-I (siYB-1)", Biomaterials, 2013, vol. 34, pp. 6882-6892.
Examination Report from the European Patent Office dated Nov. 2, 2022, in related EP application No. 19893158.6, including Search Opinion, Supplementary Search Report, and examined claims 1-10.
Vincent Aucagne et al., "Rotaxanes of Cyclic Peptides", Journal of the American Chemical Society, 2006, vol. 128, No. 6, pp. 1784-1785.

* cited by examiner

Val:Hyd= 1:0, 1:1, 0:1
NUMBER OF SCANS: 128 MEASUREMENT TEMPERATURE: 25℃
MEASUREMENT SOLVENT: DMSO-$d_6$

GENERAL VIEW OF $^1$H-NMR MEASUREMENT RESULTS IN THE CASE OF MIXING ERYTHROMYCIN (ERYTH) AND DIETHYLENETRIAMINE (DET)

ENLARGED VIEW (0. 6－1. 9ppm)
OF $^1$H-NMR MEASUREMENT RESULTS IN THE CASE OF MIXING ERYTHROMYCIN (ERYTH) AND DIETHYLENETRIAMINE (DET)

ENLARGED VIEW (2. 0−3. 0 ppm) OF $^{1}$H-NMR MEASUREMENT RESULTS IN THE CASE OF MIXING ERYTHROMYCIN (ERYTH) AND DIETHYLENETRIAMINE (DET)

ENLARGED VIEW (2. 6−3. 6 ppm) OF $^{1}$H-NMR MEASUREMENT RESULTS IN THE CASE OF MIXING ERYTHROMYCIN (ERYTH) AND DIETHYLENETRIAMINE (DET)

ENLARGED VIEW (3. 4−5. 6 ppm) OF $^1$H-NMR MEASUREMENT RESULTS IN THE CASE OF MIXING ERYTHROMYCIN (ERYTH) AND DIETHYLENETRIAMINE (DET)

GENERAL VIEW OF $^1$H-NMR MEASUREMENT RESULTS IN THE CASE OF MIXING BACITRACIN (BACI) AND DIHYDRALAZINE (DIHYD)

ENLARGED VIEW (0−1. 6ppm) OF $^1$H-NMR MEASUREMENT RESULTS IN THE CASE OF MIXING BACITRACIN (BACI) AND DIHYDRALAZINE (DIHYD)

ENLARGED VIEW (1. 3−3. 3ppm) OF $^1$H-NMR MEASUREMENT RESULTS IN THE CASE OF MIXING BACITRACIN (BACI) AND DIHYDRALAZINE (DIHYD)

ENLARGED VIEW (3. 3−5. 3 ppm) OF $^{1}$H-NMR MEASUREMENT RESULTS IN THE CASE OF MIXING BACITRACIN (BACI) AND DIHYDRALAZINE (DIHYD)

ENLARGED VIEW (6. 3−11. 3 ppm) OF $^{1}$H-NMR MEASUREMENT RESULTS IN THE CASE OF MIXING BACITRACIN (BACI) AND DIHYDRALAZINE (DIHYD)

GENERAL VIEW OF $^1$H-NMR MEASUREMENT RESULTS IN THE CASE OF MIXING BACITRACIN (BACI) AND 1-NAPHTHYLHYDRALAZINE (1-NH)

ENLARGED VIEW (0－2．1ｐｐｍ) OF $^1$H-NMR MEASUREMENT RESULTS IN THE CASE OF MIXING BACITRACIN (BACI) AND 1-NAPHTHYLHYDRALAZINE (1-NH)

ENLARGED VIEW (2. 0−4. 0 ppm) OF $^{1}$H-NMR MEASUREMENT RESULTS IN THE CASE OF MIXING BACITRACIN (BACI) AND 1-NAPHTHYLHYDRALAZINE (1-NH)

ENLARGED VIEW (4. 0−5. 5 ppm) OF $^{1}$H-NMR MEASUREMENT RESULTS IN THE CASE OF MIXING BACITRACIN (BACI) AND 1-NAPHTHYLHYDRALAZINE (1-NH)

ENLARGED VIEW (6.4−9.0ppm) OF $^1$H-NMR MEASUREMENT RESULTS IN THE CASE OF MIXING BACITRACIN (BACI) AND 1-NAPHTHYLHYDRALAZINE (1-NH)

GENERAL VIEW OF $^{1}$H-NMR MEASUREMENT RESULTS IN THE CASE OF MIXING BACITRACIN (BACI) AND DIETHYLENETRIAMINE (DET)

ENLARGED VIEW (0. 0−2. 1ppm) OF $^{1}$H-NMR MEASUREMENT RESULTS IN THE CASE OF MIXING BACITRACIN (BACI) AND DIETHYLENETRIAMINE (DET)

ENLARGED VIEW (2.1−3.1 ppm) OF $^1$H-NMR MEASUREMENT RESULTS IN THE CASE OF MIXING BACITRACIN (BACI) AND DIETHYLENETRIAMINE (DET)

ENLARGED VIEW (3.0−4.0 ppm) OF $^1$H-NMR MEASUREMENT RESULTS IN THE CASE OF MIXING BACITRACIN (BACI) AND DIETHYLENETRIAMINE (DET)

CHEMICAL SHIFT (ppm)

ENLARGED VIEW (4. 0−5. 5ppm) OF $^1$H-NMR MEASUREMENT RESULTS IN THE CASE OF MIXING BACITRACIN (BACI) AND DIETHYLENETRIAMINE (DET)

CHEMICAL SHIFT (ppm)

ENLARGED VIEW (6. 5−9. 5 ppm) OF $^1$H-NMR MEASUREMENT RESULTS IN THE CASE OF MIXING BACITRACIN (BACI) AND DIETHYLENETRIAMINE (DET)

GENERAL VIEW OF $^1$H-NMR MEASUREMENT RESULTS IN THE CASE OF MIXING VALINOMYCIN (VAL) AND DIHYDRALAZINE (DIHYD)

ENLARGED VIEW (0. 5−1. 5 ppm) OF $^1$H-NMR MEASUREMENT RESULTS IN THE CASE OF MIXING VALINOMYCIN (VAL) AND DIHYDRALAZINE (DIHYD)

ENLARGED VIEW (1.9-2.3 ppm) OF $^1$H-NMR MEASUREMENT RESULTS IN THE CASE OF MIXING VALINOMYCIN (VAL) AND DIHYDRALAZINE (DIHYD)

ENLARGED VIEW (4.1-5.3 ppm) OF $^1$H-NMR MEASUREMENT RESULTS IN THE CASE OF MIXING VALINOMYCIN (VAL) AND DIHYDRALAZINE (DIHYD)

CHEMICAL SHIFT (ppm)

ENLARGED VIEW (7. 8-8. 3 ppm)
OF $^{1}$H-NMR MEASUREMENT RESULTS IN THE CASE OF MIXING VALINOMYCIN (VAL) AND DIHYDRALAZINE (DIHYD)

Erythromycin

DELIVERY OF CYCLIC COMPOUND BY USING CARRIER

CROSS-REFERENCE

This application is the US national stage of International Patent Application No. PCT/JP2019/047900 filed on Dec. 6, 2019, which claims priority to Japanese Patent Application No. 2018-229598 filed on Dec. 7, 2018; all publications, patents, and patent applications cited therein are incorporated herein by reference in their entirety.

TECHNICAL FIELD

The present invention relates to a complex of a cyclic compound and a delivery carrier having a shaft portion for carrying the cyclic compound.

BACKGROUND ART

Hitherto, various drug delivery systems (DDSs) have been developed for the purposes of, for example, controlled release of a drug, improvement in stability thereof in blood, solubilization thereof, and reduction of side effects thereof (for example, Patent Literatures 1 and 2).

In addition, in recent years, cyclic compounds each having an inhibitory capacity to bind to and inactivate a protein have been investigated as drugs. There is a report that the cyclic compounds are structurally determined in a three-dimensional manner as compared to linear compounds, and hence are each likely to act on a binding site of a protein, consequently showing high selectivity and inhibitory capacity for the protein (Non Patent Literature 1). In addition, the cyclic compounds generally have molecular weights of from 500 to 2,000, which are between those of low-molecular-weight drugs and biomolecular drugs, and have both of membrane-penetrating properties, which are a feature of the low-molecular-weight drugs, and selective binding properties of proteins serving as the biomolecular drugs, and hence are expected to find a wide range of applications. On the other hand, the cyclic compounds are poorly soluble in water, and also lack a functional group suited for binding to a related-art delivery carrier in many cases.

Accordingly, there is a demand for development of a drug delivery system configured to solubilize a cyclic compound, and to deliver the cyclic compound to a target cell or tissue while suppressing its pharmacological activity by a non-covalent bond.

PRIOR ART LITERATURE

Patent Literature

Prior Art Literature 1: WO 2006/085664 A1
Prior Art Literature 2: WO 2009/157279 A1

Non Patent Literature

Non-Prior Art Literature 1: F. Albericio, et al. Future Med. Chem., 4 (2012) 1527-1531

SUMMARY OF THE INVENTION

The present invention has been made to solve the above-mentioned problem, and a primary object of the present invention is to provide a drug delivery system that delivers a cyclic compound to a target cell or tissue while suppressing its pharmacological activity.

According to one aspect of the present invention, there is provided a complex, including: a cyclic compound; and a delivery carrier having a shaft portion for carrying the cyclic compound, wherein the shaft portion is included in the cyclic compound to complex the cyclic compound and the delivery carrier with each other.

In one embodiment, the delivery carrier is a polymer having side chains, and at least one of the side chains has the shaft portion.

In one embodiment, the polymer has a hydrophilic polymer segment and a hydrophobic polymer segment, and a side chain of the hydrophobic polymer segment has the shaft portion.

In one embodiment, an in vivo cleavable bond is present between the shaft portion and a main chain of the polymer.

In one embodiment, the delivery carrier has: the shaft portion; and cap portions, which are arranged at both ends of the shaft portion and prevent the cyclic compound from being detached from the shaft portion.

In one embodiment, the cap portions each contain a hydrophilic polymer.

In one embodiment, an in vivo cleavable bond is present between the shaft portion and each of the cap portions.

In one embodiment, the shaft portion is a residue of at least one selected from hydralazine, dihydralazine, 1-naphthylhydralazine, and diethylenetriamine.

In one embodiment, the cyclic compound is at least one selected from valinomycin, bacitracin, and erythromycin.

According to another aspect of the present invention, there is provided a polymer particle composition, including the complex.

In the present invention, the delivery carrier having the shaft portion for carrying the cyclic compound is used, and the shaft portion is included in the cyclic compound to complex the delivery carrier and the cyclic compound with each other. Accordingly, the cyclic compound can be delivered to a target cell or tissue while its pharmacological activity is suppressed.

DETAILED DESCRIPTION OF THE EMBODIMENTS

Preferred embodiments of the present invention are described below. However, the present invention is not limited to these embodiments. In addition, the embodiments may be combined with each other as appropriate.

A. Complex

A complex according to one embodiment of the present invention includes: a cyclic compound; and a delivery carrier having a shaft portion for carrying the cyclic compound, wherein the shaft portion is included in the cyclic compound to complex the cyclic compound and the delivery carrier with each other.

A-1. Complex according to First Embodiment

Figure 1:
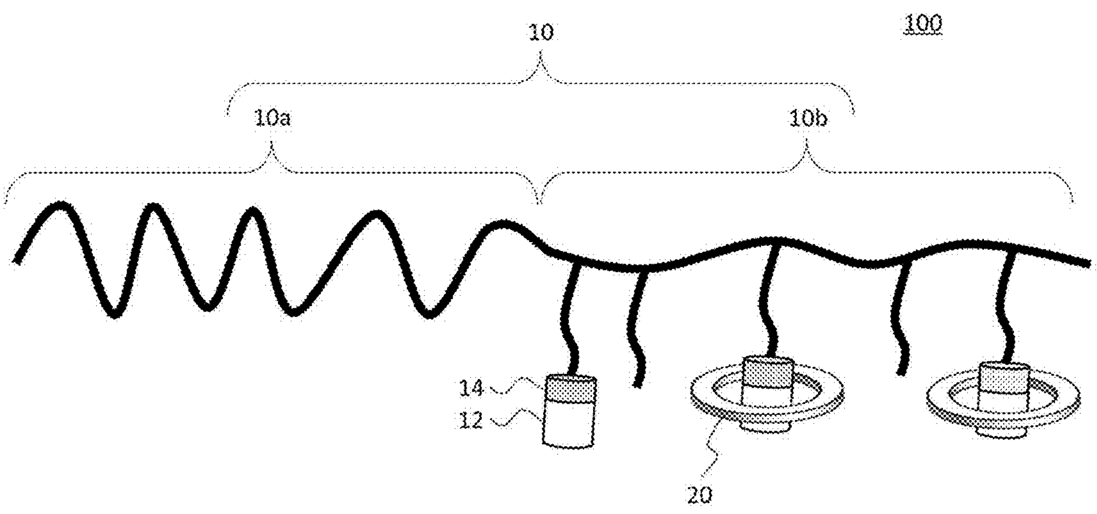
FIG. 1 is a conceptual diagram for illustrating a complex according to a first embodiment.

FIG. 1 is a conceptual diagram for illustrating a complex according to a first embodiment of the present invention. As illustrated in FIG. 1, a complex 100 is a complex of a polymer (delivery carrier) 10, which has a shaft portion 12 in a side chain thereof, and a cyclic compound 20, and the cyclic compound 20 includes the shaft portion 12 to complex the polymer 10 and the cyclic compound 20 with each other.

In the complex 100, the number of molecules of the cyclic compound 20 carried by one molecule of the polymer 10 may be, for example, from 1 to 200, preferably from 5 to 100, more preferably from 10 to 60.

In the illustrated example, the polymer 10 is a block copolymer having a hydrophilic polymer segment 10*a* and a hydrophobic polymer segment 10*b*, and only the hydrophobic polymer segment 10*b* has the shaft portion(s) 12 in (a) side chain(s) thereof. Thus, the polymer 10 shown in FIG. 1 is a diblock copolymer having (only) one hydrophilic polymer segment 10*a* and (only) one hydrophobic polymer segment 10*b*. However, the present disclosure is not limited to such embodiment. For example, a polymer formed only of a polymer segment having the shaft portion(s) in (a) side chain(s) thereof (e.g., a hydrophobic polymer segment to be described later) may be used as the delivery carrier.

In addition, in the illustrated example, an in vivo cleavable bond 14 is present between the shaft portion 12 and the main chain of the polymer. However, the present invention is not limited to such embodiment. Specifically, the shaft portion may be introduced into the side chain via or without via the in vivo cleavable bond.

In the complex of the illustrated example, the shaft portion arranged at the end of a side chain of the polymer is included in the cyclic compound. With the complex having such configuration, the cyclic compound, which has been difficult to apply to a related-art DDS, can be delivered to a target cell or tissue while its pharmacological activity is suppressed. Further, through use of a block copolymer having a hydrophilic polymer segment and a hydrophobic polymer segment as the polymer, polymeric micelles can be formed in a polar medium with the drug-carrying hydrophobic polymer segment directed inward and the hydrophilic polymer segment directed outward. Polymeric micelles having such configuration are excellent in biocompatibility and stability in blood, and hence are useful as a DDS.

A-1-1. Cyclic Compound

Any appropriate compound having desired pharmacological activity may be used as the cyclic compound. The ring of the cyclic compound has dimensions and a shape that allow the shaft portion to be included, and may be, for example, an 8- or more-membered, preferably 10- or more-membered, more preferably 12- or more-membered, still more preferably 16-membered to 50-membered homocycle or heterocycle. A heteroatom contained in the heterocycle may be, for example, oxygen or nitrogen. Each of those heteroatoms is useful from the viewpoint of exhibiting non-covalent bonding interactions (e.g., hydrogen bonding, coordinate bonding, ionic bonding, van der Waals force, or XH/π interactions (X═C, N, or O)) with the shaft portion.

Specific examples of the cyclic compound include: macrolides, such as valinomycin, aureobasidin A, HUN-7293, nonactin, rapamycin, tacrolimus, erythromycin, clarithromycin, roxithromycin, azithromycin, josamycin, rokitamycin, kitasamycin, acetylspiramycin, telithromycin, lincomycin, clindamycin, rifabutin, rifampicin, rifapentine, rifaximin, tacrolimus, pimecrolimus, pacritinib, temsirolimus, zotarolimus, everolimus, rifalazil, ridaforolimus, telithromycin, simeprevir, danoprevir, and vaniprevir; cyclic polypeptides, such as cyclosporin, microcystin, bacitracin, voclosporin, linopristin, and flopristin; crown ether; porphyrin; and cyanostar and cyclodextrin. The cyclic compounds may be used alone or in combination thereof.

A-1-2. Polymer having Shaft Portion in Side Chain(s)

Any appropriate polymer may be used as the polymer having the shaft portion(s) in (a) side chain(s) thereof. When the polymer is a block copolymer in which a hydrophilic polymer segment and a hydrophobic polymer segment are linearly linked to each other, examples of a polymer for forming the hydrophilic polymer segment include polyethylene glycol, polypropylene glycol, poly(2-oxazoline), polysaccharide, polyvinyl alcohol, polyvinylpyrrolidone, polyacrylamide, polymethacrylamide, polyacrylate, and polymethacrylate. Of those, polyethylene glycol may be preferably used. The hydrophilic polymer segment may be linear, or may be branched.

The number of repetitions of a monomer unit in the polymer for forming the hydrophilic polymer segment (in the case of a branched chain, the number of repetitions in each chain) may be, for example, from 20 to 20,000.

As a polymer for forming the hydrophobic polymer segment, there is selected a polymer having hydrophilicity lower than that of the hydrophilic polymer segment to such an extent that the block copolymer can form micelles in a state in which the hydrophilic polymer segment is directed outward and the hydrophobic polymer segment is directed inward in a polar solvent. Examples of such polymer include polyglycolic acid (PGA), polylactic acid (PLA), and a copolymer thereof (PLGA), polyamino acid, and polyether. Of those, polyamino acid may be preferably used.

Examples of the polyamino acid include poly(aspartic acid) and/or derivatives thereof (e.g., a poly(alkyl aspartate), a poly(aryl aspartate), a poly(aralkyl aspartate), and copolymers of those compounds and poly(aspartic acid)), poly (glutamic acid) and/or derivatives thereof (e.g., a poly(alkyl glutamate), a poly(aryl glutamate), a poly(aralkyl glutamide), and copolymers of those compounds and poly(glutamic acid)), and poly(lysine) and/or derivatives thereof, in which a shaft portion is introduced to at least one side chain thereof.

When the polymer for forming the hydrophobic polymer segment is a polyamino acid, the number of repetitions of amino acid residues is, for example, from 5 to 300, preferably from 10 to 250, more preferably from 20 to 200. In addition, the introduction ratio of the shaft portion (number of side chains each having shaft portion/total number of side chains in hydrophobic polymer segment×100) may be, for example, from 5% to 100%, preferably from 10% to 90%, more preferably from 30% to 70%.

The number of shaft portions that one molecule of the polymer has is 1 or more, preferably 5 or more, more preferably 10 or more, still more preferably from 15 to 150, still even more preferably from 20 to 100.

The shaft portion is a portion to be included in the cyclic compound, and has dimensions and a shape that allow its inclusion in the ring of the cyclic compound. The shaft portion preferably further has a group capable of interacting with the cyclic compound in a non-covalent bonding manner by, for example, a hydrophobic interaction or hydrogen bonding. The non-covalent bonding interaction between the shaft portion and the cyclic compound may also be referred to as so-called "host-guest interaction". The shaft portion has a structure corresponding to, for example, the size of the ring of the cyclic compound and an electrical atmosphere in the ring, and can be molecularly recognized by the cyclic compound.

The shaft portion is typically introduced into a side chain of the polymer through a reaction between a compound having the shaft portion and the side chain of the polymer. As the compound having the shaft portion, there is selected a compound having the shaft portion and a functional group that can be utilized for the reaction with the side chain of the polymer.

An example of a method of determining the compound (guest molecule) having the shaft portion with a focus on the host-guest interaction is described below.

[Method of Determining Guest Molecule]

(Step 1) The structure of the cyclic compound (host molecule) to be delivered is analyzed (e.g.: chemical structure, three-dimensional conformation, size of the ring, and the like).

(Step 2) A search is made for a guest molecule candidate (criteria: chemical structure; three-dimensional conformation; size of the molecule; presence of a donor atom having a lone pair, such as a nitrogen atom, in the molecule; presence of a functional group for introduction into a side chain of the polymer; and the like).

(Step 3) Whether the guest molecule fits into the host molecule is investigated using a molecular modeling program "Maestro" (manufactured by Schrodinger, Inc.) or the like.

(Step 4) The guest molecule (or a polymer conjugated with the guest molecule) and the host molecule are actually simply mixed with each other in water or an organic solvent to cause a host-guest interaction, to thereby find a combination for a stable host-guest complex.

The combination for forming the stable host-guest complex may be determined by, for example, a method including the following steps A and B.

(Step A) The presence of functional groups that cause mutual molecular recognition is recognized on the basis of peak shifts in a $^1$H-NMR spectrum.

(Step B) A binding constant (K) is calculated from a UV spectrum, and a search is made for a combination having a large binding constant (for example, a combination having a binding constant (association constant) of from 10 $M^{-1}$ to 1,000 $M^{-1}$, or for example, a combination having a binding constant (association constant) of from 10 $M^{-1}$ to 100 $M^{-1}$).

The method involving using the molecular modeling program "Maestro" (manufactured by Schrodinger, Inc.) has been described above as an example of the method of determining the compound (guest molecule) having the shaft portion. However, the method is not limited thereto, and the compound (guest molecule) having the shaft portion that can be included in the cyclic compound (host molecule) of interest may be determined by utilizing, for example, any of various molecular recognition technologies and molecular design technologies based on host-guest chemistry.

Examples of the combination of the cyclic compound and the shaft portion (compound having the shaft portion) that can form an inclusion complex by the host-guest interaction include valinomycin and hydralazine, valinomycin and dihydralazine, cyclosporin and dihydralazine, erythromycin and hydralazine, lorlatinib and hydralazine, β-benzyl-L-aspartic acid and rifampicin, 1,5-diaminopentane and erythromycin, diaminopentane and lorlatinib, diethylenetriamine and valinomycin, diethylenetriamine and rifampicin, diethylenetriamine and erythromycin, bacitracin and diethylenetriamine, bacitracin and dihydralazine, and bacitracin and 1-naphthylhydralazine.

The shaft portion is preferably introduced at the terminal end of the side chain via an in vivo cleavable bond. Any appropriate chemical bond that can be utilized in a DDS may be adopted as the in vivo cleavable bond. Typical examples of such bond include a disulfide bond, an acetal bond, a ketal bond, a hydrazone bond, an enol ether bond, an enol ester bond, an amide bond, an imine bond, an iminium bond, an enamine bond, a silyl ether bond, a silazane bond, a silyl enol ether bond, a diol bond, a diazo bond, an ester bond, a sulfone bond, and a silicon-carbon bond. Of those, a disulfide bond, an acetal bond, and a hydrazone bond are preferred.

The disulfide bond (—S—S—) is easily cleaved under a reducing environment. Through utilization of such characteristic, efficient drug delivery to cells can be achieved. Specifically, in a living body, due to a difference in concentration of glutathione, the extracellular environment is a non-reducing environment (about 10 μM), and the intracellular environment is a reducing environment (about 10 mM). Accordingly, the complex can maintain the form of having the shaft portion included in the cyclic compound until arrival at a cell, and after being taken up by the cell, can smoothly and efficiently release the inclusion complex of the shaft portion and the cyclic compound into the cells through cleavage of the bond between the sulfur atoms in the disulfide bond. After that, the shaft portion is detached from the inclusion complex in the cell, and hence the cyclic compound can exhibit its pharmacological activity.

Acetal bonds and hydrazone bonds are easily cleaved by a difference in pH between the inside and outside of cells. Specifically, in a living body, the extracellular pH is about 7, while the pH in late endosomes in cells is from 4 to 5. Acetal bonds and hydrazone bonds are maintained outside cells, and are easily cleaved in late endosomes in the cells. As a result, as in the case of the disulfide bond, the complex can maintain the form of having the shaft portion included in the cyclic compound until arrival at a cell, and after being taken up by the cell, can smoothly and efficiently release the inclusion complex of the shaft portion and the cyclic compound into the cell.

A specific example of the polymer is represented by the following formula (I) or (II).

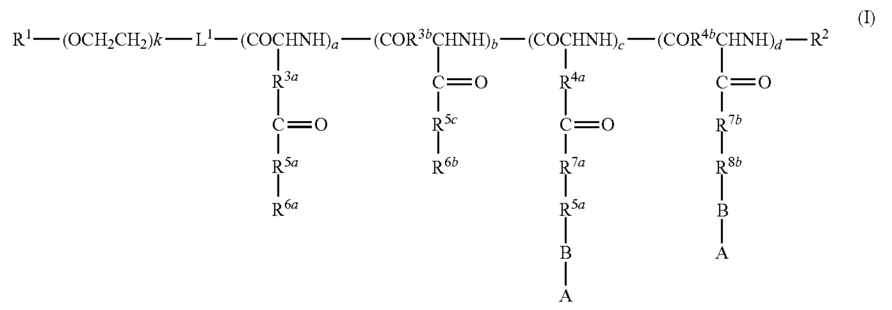

(I)

-continued

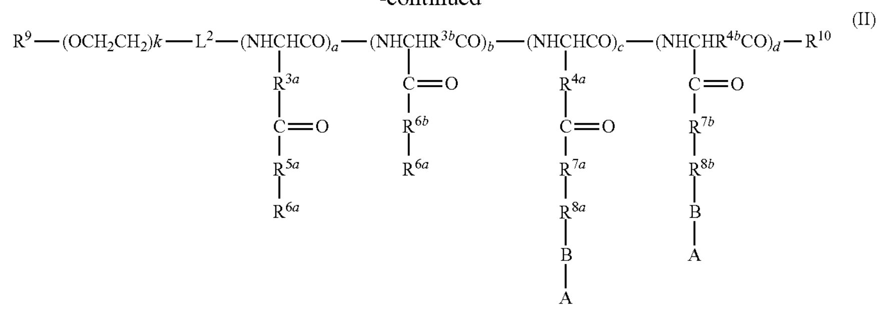

(II)

(In the formula (I) or (II), $R^1$ and $R^9$ each independently represent a hydrogen atom, or an unsubstituted or substituted linear or branched alkyl group having 1 to 12 carbon atoms, $R^2$ represents a hydrogen atom, an unsubstituted or substituted linear or branched alkyl group having 1 to 12 carbon atoms, or an unsubstituted or substituted linear or branched alkylcarbonyl group having 1 to 24 carbon atoms, $R^{3a}$, $R^{3b}$, $R^{4a}$, and $R^{4b}$ each independently represent a methylene group or an ethylene group, $R^{5a}$, $R^{5b}$, $R^{7a}$, and $R^{7b}$ each independently represent —O- or NH-, $R^{6a}$ and $R^{6b}$ each independently represent a hydrogen atom or a hydrophobic organic group, $R^{8a}$ and $R^{8b}$ each independently represent a linear or branched alkylene group having 1 to 12 carbon atoms, an arylene group having 6 to 12 carbon atoms, or a group formed of a combination thereof, $R^{10}$ represents a hydroxyl group, an oxybenzyl group, or an —O—$R^{10a}$ or —NH—$R^{10b}$ group, where $R^{10a}$ or $R^{10b}$ each independently represents an unsubstituted or substituted linear or branched alkyl group having 1 to 12 carbon atoms, $L^1$ and $L^2$ each independently represent a divalent linking group, B represents an in vivo cleavable bond, A represents a shaft portion, “k” represents an integer of from 20 to 20,000, and “a”, “b”, “c”, and “d” each independently represent an integer of from 0 to 300, provided that:

a relationship of $5 \leq a+b+c+d \leq 300$ is satisfied;

a relationship of $1 \leq c+d$ is satisfied;

the binding order of each of the amino acid repeating units is arbitrary; and $R^{6a}$, $R^{6b}$, $R^{8a}$, and $R^{8b}$ are selectable in an arbitrary manner for each amino acid repeating unit in the polymer molecule.)

Examples of the linear or branched alkyl group having 1 to 12 carbon atoms defined in each of the groups $R^1$, $R^2$, $R^9$, $R^{10a}$, and $R^{10b}$ may include a methyl group, an ethyl group, a n-propyl group, an isopropyl group, a n-butyl group, a sec-butyl group, a tert-butyl group, a n-hexyl group, a decyl group, and an undecyl group.

For a linear or branched alkyl moiety having 1 to 12 carbon atoms in the linear or branched alkylcarbonyl group having 1 to 24 carbon atoms defined in the group of $R^2$, reference may be made to the examples mentioned above, and an alkyl moiety having 13 or more carbon atoms may be exemplified by a tridecyl group, a tetradecyl group, a pentadecyl group, a nonadecyl group, a docosanyl group, and a tetracosyl group.

When the alkyl group or the alkyl moiety is “substituted”, examples of the substituent may include, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamido group, a tri-$C_{1-6}$ alkylsiloxy group, a siloxy group, and a silylamino group, or an acetalized formyl group, a formyl group, and a halogen atom, such as chlorine or fluorine. Herein, for example, an expression such as $C_{1-6}$ means having 1 to 6 carbon atoms.

The groups of $R^1$ and $R^9$ may each be substituted with a group containing a target binding site. The introduction of the target binding site at a terminal end of the hydrophilic polymer segment can improve an ability to arrive at a desired site serving as a target. The group containing a target binding site may be any appropriate group as long as the group has directivity or functionality for a tissue serving as a target, and examples thereof may include groups derived from physiologically active substances, such as an antibody or a fragment thereof, or a protein having any other functionality or target directivity, a peptide, an aptamer, a sugar, such as lactose, and folic acid, and derivatives thereof.

The hydrophobic organic group defined in each of the groups of $R^{6a}$ and $R^{6b}$ is, for example, a saturated or unsaturated linear or branched aliphatic hydrocarbon group having 6 to 27 carbon atoms, an aryl group or aralkyl group having 6 to 27 carbon atoms, or a residue derived from a sterol. A typical example of the hydrophobic organic group is a benzyl group or a phenyl group.

Examples of the linear or branched alkylene group having 1 to 12 carbon atoms, the arylene group having 6 to 12 carbon atoms, or the group formed of a combination thereof defined in each of the groups of $R^{8a}$ and $R^{8b}$ include a $C_{1-10}$ alkylene group, a $C_{6-12}$ arylene group, and a $C_{1-6}$ alkylene-$C_{6-12}$ arylene group or a $C_{1-6}$ alkylene-$C_{6-12}$ arylene-$C_{1-6}$ alkylene group, preferably a $C_{1-8}$ alkylene group, a $C_{6-10}$ arylene group, and a $C_{1-4}$ alkylene-$C_{6-10}$ arylene group or a $C_{1-4}$ alkylene-$C_{6-10}$ arylene-$C_{1-4}$ alkylene group.

The $L^1$ may represent, for example, a linking group selected from —NH—, —O—, —O—$L^{1a}$—NH—, —CO—, —$CH_2$—, and O—$L^{1a}$—S—$L^{1a}$—NH- (where $L^{1a}$s each independently represent an alkylene group having 1 to 6 carbon atoms).

The $L^2$ may represent, for example, a linking group selected from —OCO—$L^{2a}$—CO- and NHCO—$L^{2a}$—CO- (where $L^{2a}$ represents an alkylene group having 1 to 6 carbon atoms).

The B represents preferably an acetal bond, a hydrazone bond, or a disulfide bond, more preferably a hydrazone bond.

“a”, “b”, “c”, and “d”, which represent the numbers of repetitions of the respective amino acid residues, each independently represent preferably an integer of from 0 to 200, more preferably an integer of from 0 to 100. In addition, the polymerization degree (a+b+c+d) of the polyamino acid is preferably an integer of from 10 to 250, more preferably an integer of from 20 to 200. In addition, the total number (c+d) of side chains each having the shaft portion is preferably 5 or more, more preferably 10 or more, still more preferably from 15 to 150, still even more preferably from 20 to 100.

"k", which represents the number of repetitions of ethylene glycol, represents an integer of preferably from 50 to 2,000, more preferably from 100 to 1,000.

The polymer represented by the formula (I) or (II) may be synthesized by any appropriate method. As an example, a synthesis method for a polyethylene glycol-poly(benzyl aspartate) block copolymer having the shaft portion introduced into at least one side chain thereof via a hydrazone bond is described below. First, through use of polyethylene glycol having a primary amino group at an end thereof as an initiator, β-benzyl-L-aspartate-N-carboxylic anhydride is polymerized to synthesize a polyethylene glycol-poly(β-benzyl-L-aspartate) block copolymer. Then, transesterification or aminolysis is performed with a compound having a hydroxyl group or an amino group and a carbonyl group to introduce the carbonyl group into a side chain of the copolymer. Alternatively, transesterification or aminolysis may be performed with a compound having a hydroxyl group or an amino group and an acetal group, followed by the conversion of the acetal group into a carbonyl group under an acid catalyst. After that, the carbonyl group is allowed to react with a hydralazine derivative serving as the compound having the shaft portion. Thus, the block copolymer having the shaft portion introduced into at least one side chain thereof via a hydrazone bond may be obtained.

A-1-3. Preparation Method for Complex

The complex may be prepared by, for example, adding a water-soluble organic solvent capable of dissolving the polymer having the shaft portion(s) in (a) side chain(s) thereof to the polymer to dissolve the polymer, and then adding the cyclic compound, followed by dialysis against an aqueous medium, such as water or a buffer. In this case, examples of the water-soluble organic solvent include methanol, ethanol, acetonitrile, dimethyl sulfoxide, N,N-dimethylformamide, and N,N-dimethylacetamide. The mixing ratio between the polymer having the shaft portion in a side chain thereof and the cyclic compound may be appropriately set depending on purposes. The mixing ratio may be, for example, set to a ratio at which the shaft portion and the cyclic compound can efficiently form a complex through use of Job's plot method. The molar ratio of the cyclic compound to the shaft portion in the mixture may be set to, for example, 0.1 to 5.0, preferably 0.2 to 2.0 with respect to 1 mol of the shaft portion.

In the preparation method, the carrying ratio of the cyclic compound (number of molecules of cyclic compound carried by one molecule of polymer/number of shaft portions in one molecule of polymer×100) may be, for example, 10% or more, preferably 20% or more, more preferably from 40% to 100%.

A-2. Complex according to Second Embodiment

Figure 2:
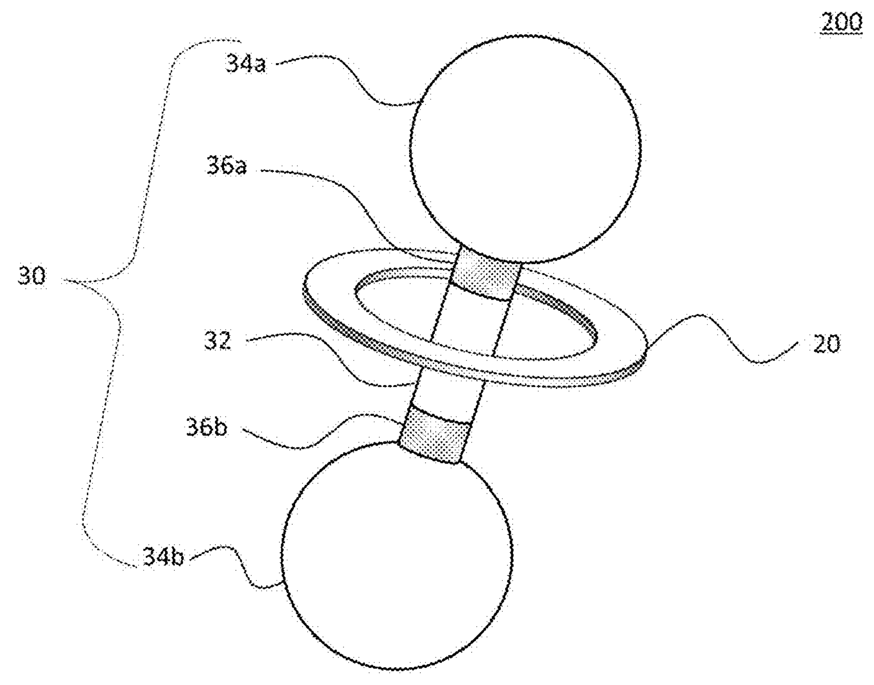
FIG. 2 is a conceptual diagram for illustrating a complex according to a second embodiment.
Figure 3A:
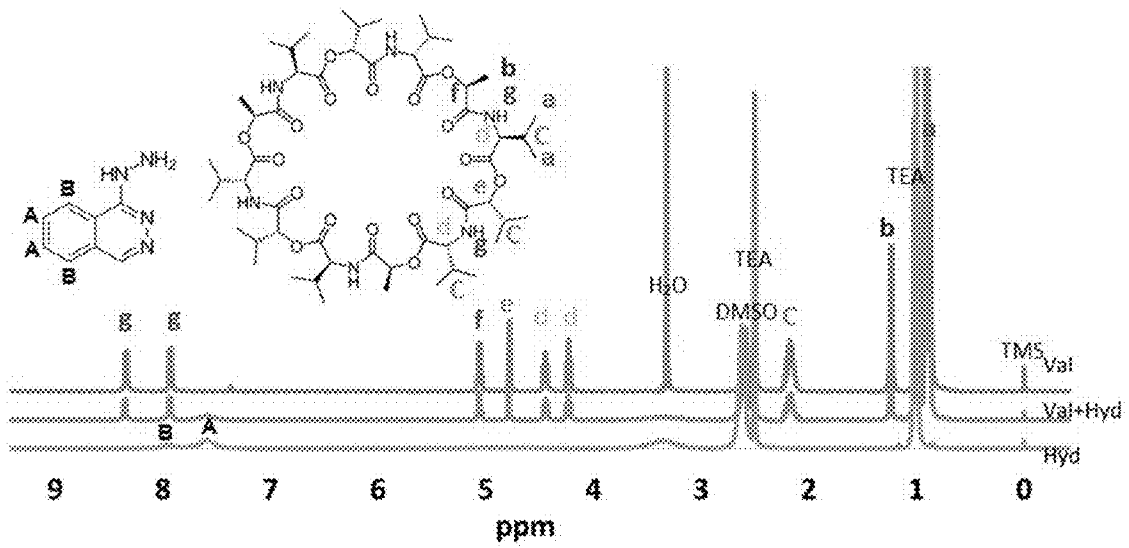
FIG. 3A is a chart showing the results of evaluation of a host-guest interaction between valinomycin and hydralazine by $^{1}$H-NMR.
Figure 3B:
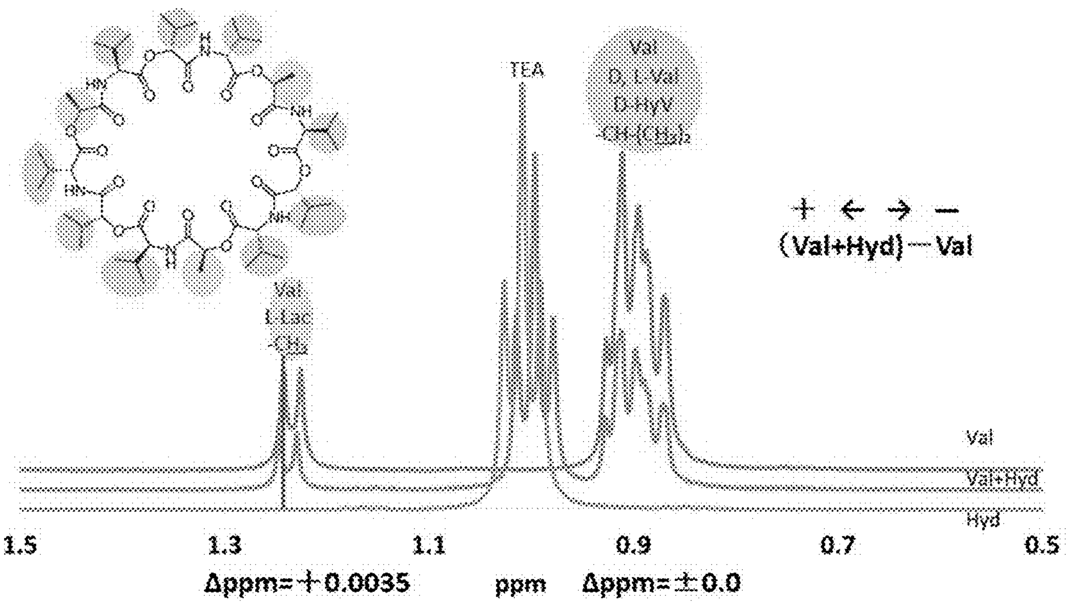
FIG. 3B is a chart showing the results of evaluation of a host-guest interaction between valinomycin and hydralazine by $^{1}$H-NMR.
Figure 3C:
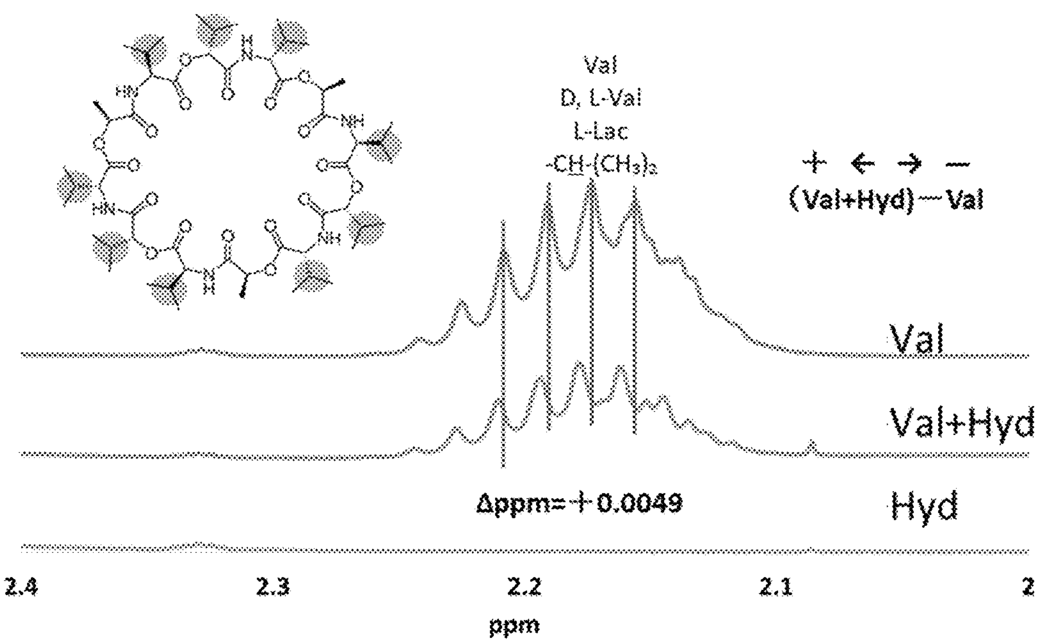
FIG. 3C is a chart showing the results of evaluation of a host-guest interaction between valinomycin and hydralazine by $^{1}$H-NMR.
Figure 3D:
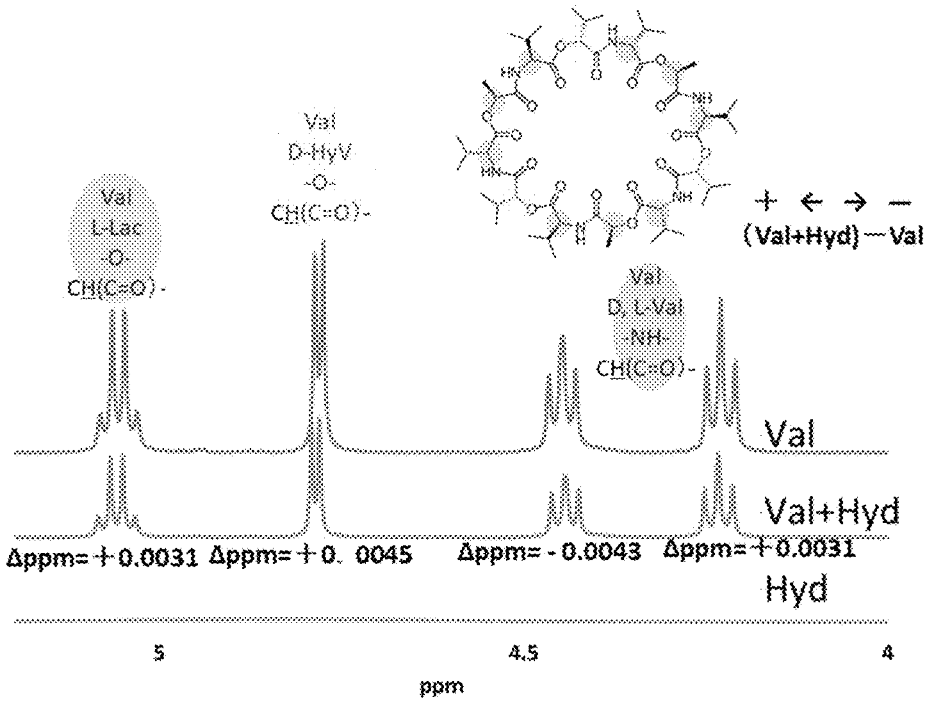
FIG. 3D is a chart showing the results of evaluation of a host-guest interaction between valinomycin and hydralazine by $^{1}$H-NMR.
Figure 3E:
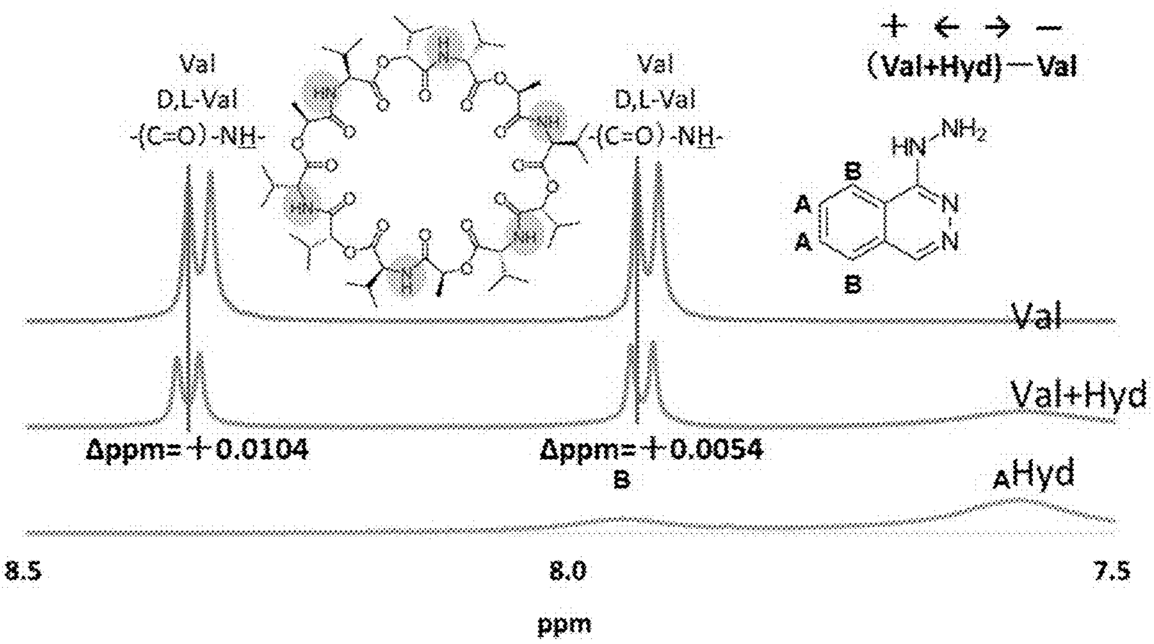
FIG. 3E is a chart showing the results of evaluation of a host-guest interaction between valinomycin and hydralazine by $^{1}$H-NMR.

FIG. 2 is a conceptual diagram for illustrating a complex according to a second embodiment of the present invention. As illustrated in FIG. 2, complex 200 is a complex of: a delivery carrier 30 having a shaft portion 32 and cap portions 34*a* and 34*b* arranged on both end sides thereof; and the cyclic compound 20, and the delivery carrier 30 and the cyclic compound 20 are complexed with each other by the cyclic compound 20 including the shaft portion 32, and the cap portions 34*a* and 34*b* preventing the cyclic compound 20 from being detached from the shaft portion 32.

In the complex 200, the number of molecules of the cyclic compound 20 carried by one molecule of the delivery carrier 30 may be 1 or 2 or more.

In the illustrated example, in vivo cleavable bonds 36*a* and 36*b* are present between the shaft portion 32 and the cap portion 34*a* and between the shaft portion 32 and the cap portion 34*b*, respectively. However, the present invention is not limited to such embodiment. For example, the in vivo cleavable bond may be present only between the shaft portion and any one of the cap portions. Alternatively, the cap portions may be directly bonded to the shaft portion without via the in vivo cleavable bonds.

In the complex according to the second embodiment, the shaft portion is included in the cyclic compound, and the cap portions can prevent the cyclic compound from being detached from the shaft portion. With the complex having such configuration, the cyclic compound, which has been difficult to apply to a related-art DDS, can be delivered to a target cell or tissue while suppressing its pharmacological activity. In addition, with the complex having such configuration, when bulky cap portions are adopted, the complex can be stably present in blood alone without undergoing secondary association to form aggregates, such as micelles, and hence can be expected to exhibit excellent tissue penetrating properties due to its small size. In the complex according to the second embodiment, the inclusion of the shaft portion by the cyclic compound may be performed through utilization of a host-guest interaction using the cyclic compound as a host molecule and the shaft portion as a guest molecule as in the complex according to the first embodiment.

A-2-1. Cyclic Compound

Examples of the cyclic compound include the cyclic compounds described in the section A-1-1.

A-2-2. Delivery Carrier

The delivery carrier has the shaft portion and preferably the cap portions bonded at both ends thereof directly or via in vivo cleavable bonds.

The cap portions preferably have such bulkiness as to be capable of preventing the cyclic compound from being detached from the shaft portion. Examples of a material for forming each of the cap portions include hydrophilic polymers, such as polyethylene glycol, polypropylene glycol, poly(2-oxazoline), polysaccharide, polyvinyl alcohol, polyvinylpyrrolidone, polyacrylamide, polymethacrylamide, polyacrylate, and polymethacrylate. Of those, polyethylene glycol may be preferably used from the viewpoints of, for example, being excellent in biocompatibility and having a large spread of molecular chains in a polar solvent. The hydrophilic polymer may be linear, or may be branched.

The number of repetitions of a monomer unit in the hydrophilic polymer (in the case of a branched chain, the number of repetitions in each chain) is, for example, from 20 to 20,000, preferably from 200 to 2,000, more preferably from 400 to 1,000.

The shaft portion is a portion to be included in the cyclic compound, and has dimensions and a shape that allow its inclusion in the ring of the cyclic compound. The shaft portion preferably further has a group capable of interacting with the cyclic compound in a non-covalent bonding manner by, for example, a hydrophobic interaction or hydrogen bonding. The non-covalent bonding interaction between the shaft portion and the cyclic compound may also be referred to as so-called "host-guest interaction". The shaft portion has a structure corresponding to, for example, the size of the ring of the cyclic compound and an electrical atmosphere in the ring, and can be molecularly recognized by the cyclic compound.

The shaft portion is typically introduced into the delivery carrier through a reaction between a compound having the shaft portion and the material for forming each of the cap portions (e.g., the hydrophilic polymer). As the compound having the shaft portion, there is selected a compound having the shaft portion and functional groups that are arranged at two sites between which the shaft portion is interposed, and that can be utilized for the reaction with the material for forming each of the cap portions. A method similar to the method described in the section A-1-2 may be used as a method of determining the compound having the shaft portion.

The in vivo cleavable bonds are as described in the section A-1-2.

A-2-3. Preparation Method for Complex

The complex may be prepared by any appropriate method. For example, a complex of a delivery carrier, which has a shaft portion and polyethylene glycol bonded to each of both ends thereof via a hydrazone bond, and a cyclic compound may be prepared by adding and mixing the cyclic compound, polyethylene glycol having an aldehyde group at one end thereof, and a dihydralazine compound serving as the compound having the shaft portion into a water-soluble organic solvent to cause a reaction, followed by dialysis against an aqueous medium, such as water or a buffer. Examples of the water-soluble organic solvent include methanol, ethanol, acetonitrile, dimethyl sulfoxide, N,N-dimethylformamide, and N,N-dimethylacetamide. The mixing ratio among the compound having the shaft portion, the cyclic compound, and the polyethylene glycol may be appropriately set depending on purposes. The mixing ratio may be set, for example, so that the molar ratio of the cyclic compound to the compound having the shaft portion in the mixture may be from 0.1 to 5.0, preferably from 0.2 to 2.0, and so that the molar ratio of the polyethylene glycol to the compound having the shaft portion may be from 1.0 to 5.0, preferably from 1.0 to 2.0, with respect to 1 mol of the shaft portion.

B. Polymer Particle Composition

A polymer particle composition according to one embodiment of the present invention contains the complex described in the section A-1. The complex can suitably form polymer particles by associating in a polar medium. For example, when the delivery carrier for forming the complex is a block copolymer having a hydrophilic polymer segment and a hydrophobic polymer segment, the complex can form polymeric micelles with the cyclic compound-carrying hydrophobic polymer segment directed inward and the hydrophilic polymer segment directed outward. In the present invention, aggregates each of which is formed through aggregation of a plurality of the complexes into a particle form are also encompassed in the particles, and such aggregates are also referred to as "polymer particles".

The average particle diameter of the polymer particles is, for example, 1,000 nm or less, preferably 400 nm or less, 200 nm or less, 150 nm or less, 100 nm or less, or 80 nm or less, and is, for example, 20 nm or more, or 30 nm or more. The average particle diameter of the particles may be measured using a commercially available dynamic light scattering (DLS) measurement apparatus.

The polymer particle composition may contain any other polymer in addition to the complex described in the section A-1 as long as the effect of the present invention is obtained. An example of such other polymer is a block copolymer having a hydrophilic polymer segment and a hydrophobic polymer segment. Such block copolymer can suitably associate in a polar medium to form stable polymer particles (e.g., polymeric micelles), and hence the coexistence thereof can provide a polymer particle composition excellent in stability. Such effect can be particularly suitably exhibited in a polymer particle composition containing a complex using as its delivery carrier a polymer having no hydrophilic polymer chain segment. Examples of the above-mentioned other block copolymer include polymers described in WO 2007/099660 A1, WO 2007/099661 A1, WO 2010/093036 A1, WO 2012/096399 A1, WO 2014/133172 A1, and WO 2015/170757 A1.

The polymer particle composition may be prepared by any appropriate method. For example, the polymer particle composition may be prepared by adding and mixing the polymer having the shaft portion in a side chain thereof, the cyclic compound, and the other polymer serving as an optional component into a water-soluble organic solvent to cause association, followed by dialysis against an aqueous medium, such as water or a buffer. Examples of the water-soluble organic solvent include methanol, ethanol, acetonitrile, dimethyl sulfoxide, N,N-dimethylformamide, and N,N-dimethylacetamide.

C. Use Method

The complex described in the section A and the polymer particle composition described in the section B are each administered to an individual in need of treatment with the carried cyclic compound. An example of an individual to be subjected to the administration is a human or a non-human mammal. A method for the administration is preferably parenteral administration, and examples thereof may include subcutaneous administration, intramuscular administration, intravenous administration, intraperitoneal administration, and intrathecal administration.

EXAMPLES

The present invention is specifically described below by way of Examples. However, the present invention is not limited to these Examples.

[Test Example 1] Evaluation of Interaction between Valinomycin (Val) and Hydralazine (Hyd) by $^1$H-NMR Val was selected as a cyclic compound, and analysis of its structure using the molecular modeling program "Maestro" (manufactured by Schrodinger, Inc.) found that the diameter of its ring was 6 Å. A search was made for a guest molecule (shaft portion) candidate capable of causing a host-guest interaction with Val under the criteria of having a molecular diameter of less than 6 Å, having a donor atom having a lone pair, such as a nitrogen atom, in the molecule, having a hydrophobic functional group for a hydrophobic interaction, and having a primary amine for introduction into a side chain of a polymer via a pH-responsive functional group, and as a result, Hyd was selected.

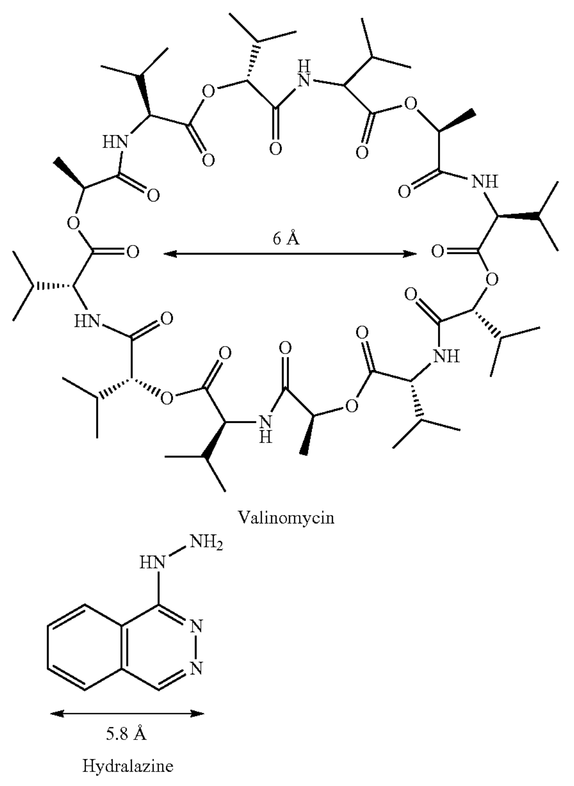

Valinomycin

Hydralazine

Then, an interaction between Val and Hyd was evaluated as described below. Val (10 mg/mL) and Hyd (1.44 mg/mL) were mixed with each other in deuterated DMSO, chemical shifts were measured by $^{1}$H-NMR, and each peak was attributed. As a control, the chemical shifts of each of valinomycin (10 mg/mL) alone and hydralazine (1.44 mg/mL) alone were also measured, and each peak was attributed. Further, in a comparison between the case of valinomycin alone and the case of coexisting with hydralazine, for changes in chemical shifts, the amounts of the changes were determined. The results are shown in FIG. 3A to FIG. 3E and Table 1.

TABLE 1

| Attributed peak | ppm | Δppm |
|---|---|---|
| (—NH—) (Val) (left) | 8.4 | +0.0100 |
| (—NH—) (Val) (right) | 7.9 | +0.0054 |
| —CH—$(CH_3)_2$ | 2.1 | +0.0049 |
| (—O—CH(C═O)—) (HyV) | 4.7 | +0.0045 |
| (—CH—) (Val) (left) | 4.4 | −0.0043 |
| Methyl groups (Lac) | 1.1 | +0.0035 |
| CH(C═O) (Lac) | 5.1 | +0.0031 |
| (—CH—) (Val) (right) | 4.3 | +0.0031 |
| Isopropyl groups | 0.9 | ±0 |

As shown in Table 1, chemical shift changes of from 0 ppm to 0.01 ppm were observed between the case of valinomycin existing alone and the case of coexisting with hydralazine. This reveals that valinomycin is influenced by hydralazine, and valinomycin and hydralazine interact with each other. In addition, rotating frame nuclear Overhauser effect spectroscopy (ROESY) measurement for detecting nearby protons between compounds was performed, and as a result, cross peaks due to proximity between the hydrogen of the amines of valinomycin and the hydrogen of the benzene ring of hydralazine were observed.

[Test Example 2] Optimization of Mixing Ratio between Val and Hyd by UV-Vis Method Val (10 mg/mL) and Hyd (1.44 mg/mL) were dissolved in acetonitrile, and were mixed with each other at various mixing ratios ([Val]:[Hyd]=9:1, 8:2, 7:3, 6:4, 5:5, 4:6, 3:7, 2:8, and 1:9). After that, spectra of the solutions based on a UV-Vis method were measured, and the mixing ratio at which Val and Hyd interacted with each other most efficiently was determined from the absorbance at 272 nm by Job's plot method. Specifically, a difference between the absorbance of each of the solutions and the absorbance of a control solution (valinomycin solution) was calculated, and the molar fraction of valinomycin in the solution at which the product of the difference and the molar fraction took the maximum value was calculated. The result was as follows: the mixing ratio ([Val]:[Hyd]) at which Val and Hyd interacted with each other most efficiently was 1:1.22.

[Test Example 3] Synthesis of Poly(ethylene glycol)-poly (β-benzyl-L-aspartate) (PEG-PBLA)

PEG-$NH_2$ (PEG molecular weight: 12 kDa) was dissolved in dichloromethane (DCM, 66 mg/mL), and β-benzyl-L-aspartic acid-N-carboxyanhydride (BLA-NCA, 60 equivalents) dissolved in a DCM/N,N-dimethylformamide (DMF) mixed solvent ([DCM]/[DMF]=10, 66 mg/mL) was added. After a reaction at 35° C. for 3 days, the reaction solution was added to diethyl ether, followed by drying under reduced pressure to afford PEG-PBLA (PBLA polymerization degree: 40). $^{1}$H-NMR in deuterated DMSO found that the yield was 68%.

[Test Example 4] Synthesis of PEG-PBLA-Acetyl (PEG-PBLA-Ac)

PEG-PBLA was dissolved in DMF (10 mg/mL), and N,N-dimethyl-4-aminopyridine (DMAP, 10 equivalents), triethylamine (TEA, 1 equivalents), and acetic anhydride (10 equivalents) were added. After a reaction at room temperature for 3 hours, the reaction solution was added to diethyl ether, followed by drying under reduced pressure to afford PEG-PBLA-Ac. $^{1}$H-NMR in deuterated DMSO found that the yield was 81%.

[Test Example 5] Synthesis of PEG-poly(aspartate-benzyl aldehyde) (PEG-P(Asp-BA)) PEG-PBLA-Ac was dissolved in DMF (60 mg/mL), and 4,4-dimethoxymethylphenylmethanamine was added. After a reaction at 35° C. for 4 days, 1 M HCl solution (100 μL) was added to the reaction solution, and a reaction was performed at room temperature for 1 hour. After that, the reaction solution was dialyzed (MWCO: 6,000 to 8,000) against pure water, followed by freeze-drying to afford PEG-P(Asp-BA). $^{1}$H-NMR in deuterated DMSO found that the introduction ratio of BA was 63%.

[Test Example 6] Synthesis of PEG-poly(Asp-benzyl hydralazine) (PEG-P(Asp-BH))

PEG-P(Asp-BA) was dissolved in DMSO (20 mg/mL), and triethylamine (170 equivalents) and Hyd (170 equivalents) were added. After a reaction at 35° C. for 4 days, the reaction solution was dialyzed (MWCO: 6,000 to 8,000) against methanol, followed by drying under reduced pressure and freeze-drying to afford PEG-P(Asp-BH) shown below. $^{1}$H-NMR in deuterated DMSO found that the introduction ratio of Hyd was 63%.

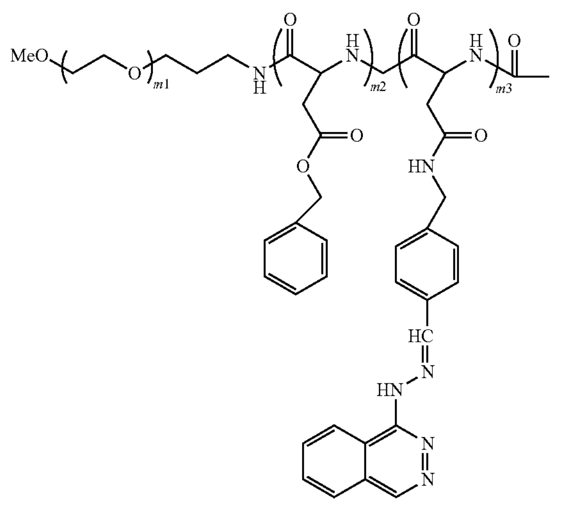

(In the formula, m2=15 and m3=25)

[Test Example 7] Synthesis of PEG-P(Asp-aliphatic ketone) (PEG-P(Asp-AK))

PEG-PBLA-Ac was dissolved in DMF (60 mg/mL), and 4,4-dimethoxypentan-1-amine was added. After a reaction at 35° C. for 4 days, 1 M HCl solution (100 μL) was added to the reaction solution, and a reaction was performed at room temperature for 1 hour. After that, the reaction solution was dialyzed (MWCO: 6,000 to 8,000) against pure water, followed by freeze-drying to afford PEG-P(Asp-AK). $^1$H-NMR in deuterated DMSO found that the introduction ratio of AK was 87%.

[Test Example 8] Synthesis of PEG-P(Asp-aliphatic hydrazine) (PEG-P(Asp-AH))

PEG-P(Asp-AK) was dissolved in DMSO (20 mg/mL), and triethylamine (170 equivalents) and Hyd (170 equivalents) were added. After a reaction at 35° C. for 4 days, the reaction solution was dialyzed (MWCO: 6,000 to 8,000) against methanol, followed by drying under reduced pressure and freeze-drying to afford PEG-P(Asp-AH) shown below. $^1$H-NMR in deuterated DMSO found that the introduction ratio of AH was 88%.

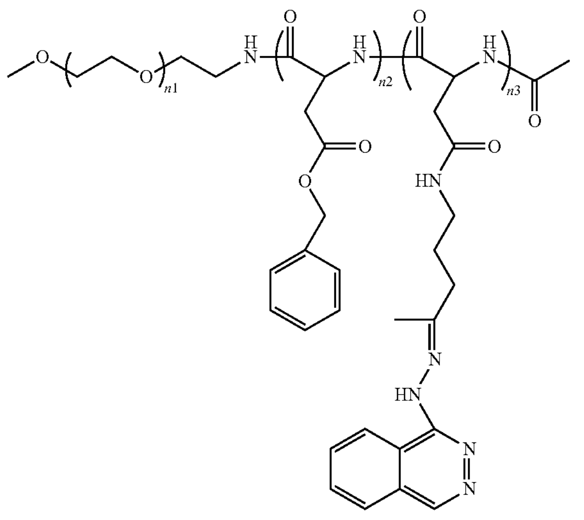

(In the formula, n2=10 and n3=28)

[Test Example 9] Preparation of Val-encapsulating Polymeric Micelles

PEG-PBLA, PEG-P(Asp-BH), or PEG-P(Asp-AH) was dissolved in N,N-dimethylacetamide (DMAc, 0.5 mg/mL), and Val ([Val]/[AH]=0, 0.3, 0.5, or 1.0, or [Val]/[BH]=0, 0.25, or 0.75) was added. After stirring at room temperature for 24 hours, the resultant was dialyzed (MWCO: 6,000 to 8,000) against a 10 mM phosphate buffer (pH 8.0) and purified through a filter. The particle diameter and polydispersity of the resultant polymeric micelles were evaluated by a dynamic light scattering (DLS) method. The results are shown in Table 2.

[Test Example 10] Evaluation of Drug-carrying Amount of Val-encapsulating Polymeric Micelles The micelles were collected by freeze-drying from the polymeric micelle solution (1 mL, 0.5 mg/mL) obtained in Test Example 9, and were dissolved in acetonitrile (0.5 mg/mL). After ultrasonic crushing for 30 minutes, the solution was added to diethyl ether, and the filtrate was dried under reduced pressure to afford Val. Then, for each polymeric micelle sample using PEG-P(Asp-BH), a drug-carrying amount (Val-carrying amount (mg) per 1 mg of the polymer) was calculated by $^1$H-NMR. Meanwhile, for each polymeric micelle sample using PEG-P(Asp-AH), a drug-carrying amount (Val-carrying amount (mg) per 1 mg of the polymer) was calculated from a UV absorbance at 220 nm in acetonitrile. In addition, the ratio of the amount of Val carried by the polymer to the addition amount of Val at the time of the preparation of the micelles was calculated as drug-carrying efficiency (%). The results are shown in Table 2.

TABLE 2

| | Val equivalent | Particle diameter (d, nm) | PDI | Drug-carrying (Val % mg/ Polymer mg) | Drug-carrying amount efficiency (%) |
|---|---|---|---|---|---|
| PEG-P(Asp AH) | 0 | 61 | 0.13 | 0 | — |
| | 0.3 | 55 | 0.14 | 7.0 | 19 |
| | 0.5 | 53 | 0.23 | 7.4 | 12 |
| | 1.0 | 51 | 0.23 | 4.5 | 4.0 |
| PEG-P(Asp-BH) | 0 | 47 | 0.06 | 0 | — |
| | 0.25 | 45 | 0.06 | 2 | — |
| | 0.75 | 48 | 0.1 | 5 | — |

As shown in Table 2, the Val-encapsulating polymeric micelles were unimodal particles having particle diameters of from about 45 nm to about 60 nm. In addition, it was recognized that the polymeric micelles obtained by adding 0.3 equivalent of Val most efficiently carried Val. Meanwhile, in the micelles ([Val]/[Asp]=0.3:1) prepared from PEG-PBLA having no Hyd residue in the side chain structure, the encapsulation of valinomycin was not confirmed. Encapsulation into the micelles through an interaction between the Hyd residue and valinomycin was implicated by this.

[Test Example 11] Stability Test of Val-encapsulating Polymeric Micelles under Physiological Condition A Val-encapsulating polymeric micelle solution (1 mg/mL) prepared by adding 0.3 equivalent of Val to PEG-P(Asp-BH) was dialyzed (MWCO: 3,500) against a 10 mM phosphate buffer (pH 7.4, 5.5, or 3.0), and polymer-derived scattering intensities at various times (after 1, 3, 6, and 24 hours) were measured by a DLS method. The results are shown in FIG. 4.

Figure 4:
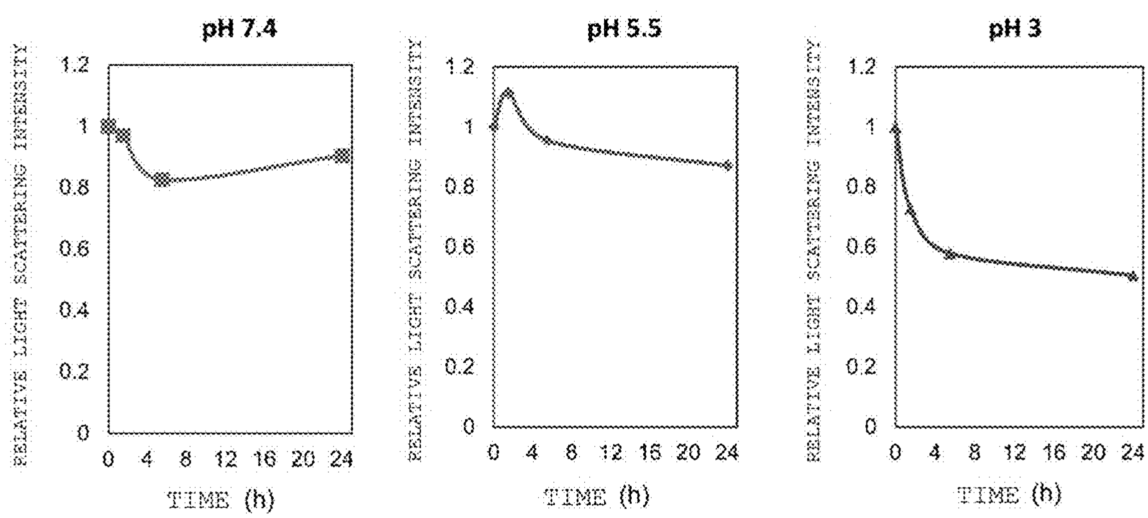
FIG. 4 includes graphs showing the results of a stability test of valinomycin-encapsulating polymeric micelles.

As shown in FIG. 4, the Val-encapsulating polymeric micelles showed high stability under the conditions of a pH of 7.4 and a pH of 5.5.

[Test Example 12] Evaluation of Val Release Rate of Val-encapsulating Polymeric Micelles A Val-encapsulating polymeric micelle solution (2 mL, 0.5 mg/mL) prepared by adding 0.3 equivalent of Val to PEG-P(Asp-AH) was dialyzed (MWCO: 3,500) against a 10 mM phosphate buffer (pH 7.4 or 5.0), and Val amounts in the external solution at various times (after 1, 3, 6, and 24 hours) were measured by an HPLC method. The ratio of the amount of Val released into the external solution to the amount of Val carried by the micelles was calculated as a release rate. The results are shown in FIG. 5.

Figure 5:
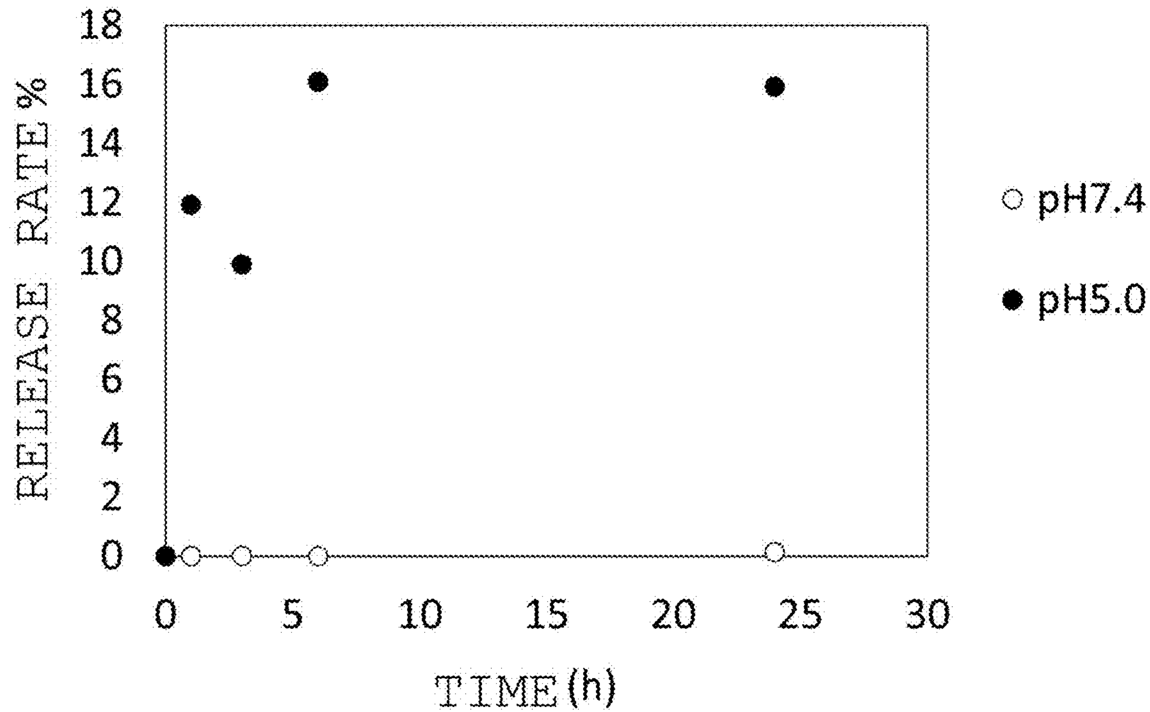
FIG. 5 is a graph showing the results of evaluation of the valinomycin release rate of valinomycin-encapsulating polymeric micelles.

As shown in FIG. 5, the Val-encapsulating polymeric micelle solution stably carried Val at physiological pH (7.4), but released Val at endosomal pH (5.0).

[Test Example 13] Toxicity Test of Val-encapsulating Polymeric Micelles against Cultured Cells Human pancreatic adenocarcinoma cells (B×PC3 cells, Panc-cells, or MiaPaCa cells) were seeded into a 96-well plate (5,000 cells/well). After 24 hours, a Val-encapsulating polymeric micelle solution prepared by adding 0.3 equivalent of Val to PEG-P(Asp-BH) or Val alone was added at various Val concentrations. After 48 hours, the cells were washed with PBS, and a medium was added. After that, Cell Counting Kit-8 (CCK-8, 10 μL/well) was added to the medium, and 30 minutes later, UV absorbance at 450 nm was measured. The cell survival rate was calculated from the absorbance between 100% for a group in which only the buffer was added in place of the drug and 0% for a cell-free group, and an $IC_{50}$ (Val concentration) was determined.

The results are shown in Table 3.

TABLE 3

| Cells | Drug | $IC_{50}$ (nM) |
|---|---|---|
| BxPC3 | Val alone | 12.5 |
| | Val-encapsulating polymeric micelles | 155 |
| PANC-1 | Val alone | 8.3 |
| | Val-encapsulating polymeric micelles | 140 |
| MiaPaCa | Val alone | 23.2 |
| | Val-encapsulating polymeric micelles | 134 |

As shown in Table 3, it is found that, by virtue of the encapsulation of Val in the polymeric micelles, the release of valinomycin was controlled, and its toxicity was suppressed.

[Test Example 14] Evaluation of Blood Retentivity and Tissue-penetrating Properties of Val-encapsulating Polymeric Micelles A Val-encapsulating polymeric micelle solution prepared by using PEG-P(Asp-BH)-Cy5 fluorescently labeled with Cy5 and 0.3 equivalent of Val was intravenously administered (administration amount of Val: 1.5 mg/kg) to the tail vein of subcutaneous tumor model mice (B×PC3), and fluorescence intensities in the vein and the tumor tissue were measured by intravital confocal laser scanning microscopy (IV-CLSM). Blood retentivity was evaluated between 0 for the fluorescence intensity before the administration of the micelles and 100 for the fluorescence intensity immediately after the administration. The results are shown in FIG. 6.

Figure 6:
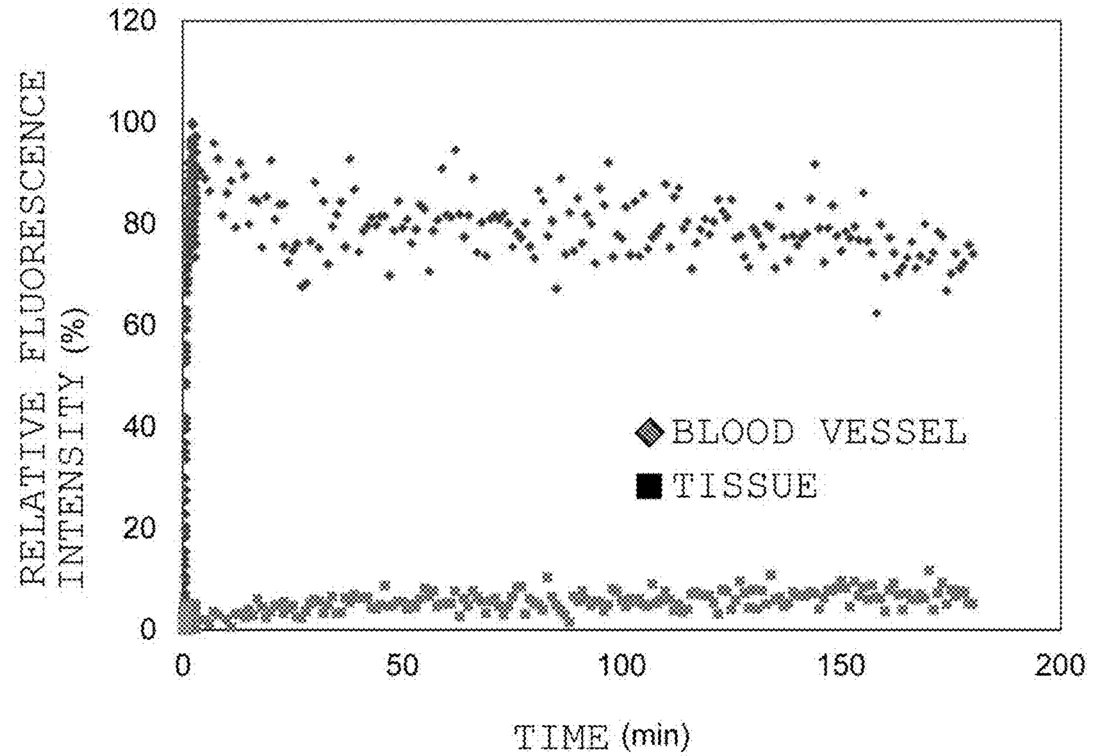
FIG. 6 is a graph showing the results of evaluation of the blood retentivity and tissue-penetrating properties of valinomycin-encapsulating polymeric micelles.

As shown in FIG. 6, it is found that the Val-encapsulating polymeric micelles show high stability in blood, and penetrate the tissue over time.

[Test Example 15] Evaluation of Biodistribution of Val-encapsulating Polymeric Micelles A Val-encapsulating polymeric micelle solution prepared by using PEG-P(Asp-BH)-Cy5 fluorescently labeled with Cy5 and 0.3 equivalent of Val was intravenously administered (administration amount of Val: 1.5 mg/kg) to the tail vein of subcutaneous tumor model mice (B×PC3), and the fluorescence intensity in the tumor was observed over time by IV-CLSM. In addition, organs (liver, kidneys, spleen, heart, and lung) and the tumor were removed 24 hours after the administration, and fluorescence intensities in the collected organs and tumor were measured by IVIS. The temporal fluorescence intensity in the tumor is shown in FIG. 7(*a*), and the fluorescence intensities in the collected organ and tumor are shown in FIG. 7(*b*).

Figure 7:
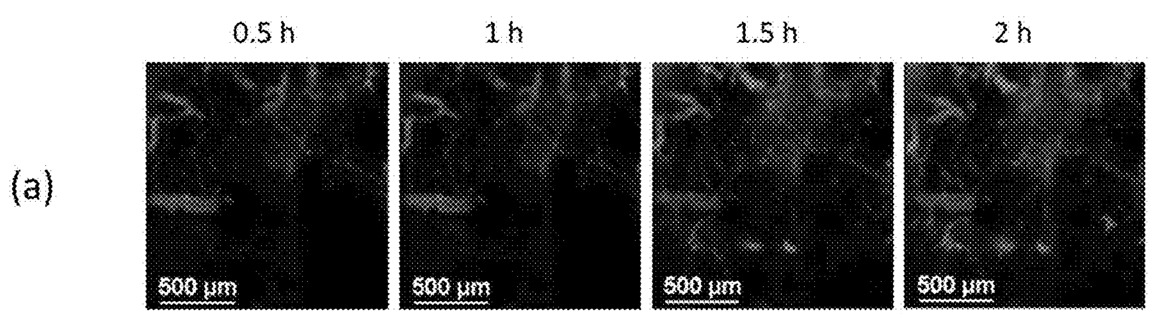
FIGS. 7 show the results of evaluation of the biodistribution of valinomycin-encapsulating polymeric micelles.
Figure 7:
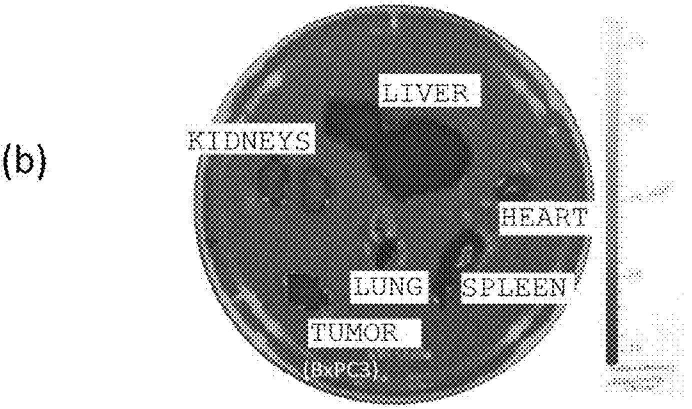

As shown in FIG. 7(*a*), it is found that the Val-encapsulating polymeric micelles accumulate in the tumor over time. In addition, as shown in FIG. 7(*b*), the accumulation of the micelles in the tumor was confirmed 24 hours after the administration.

[Test Example 16] Evaluation of Antitumor Effect of Val-encapsulating Polymeric Micelles on Tumor-bearing Mice A Val-encapsulating polymeric micelle solution prepared by using PEG-P(Asp-BH) (administration amount of Val: 1.5 mg/kg), a valinomycin solution (1.5 mg/kg), or a gemcitabine solution (80 mg/kg) was intravenously administered (only the valinomycin solution was intraperitoneally administered) to the tail vein of subcutaneous tumor model mice (B×PC3) on day 0, day 2, and day 4, and the sizes of the tumors and the body weights of the mice after lapses of various times were measured (n=4). The results are shown in FIG. 8.

Figure 8:
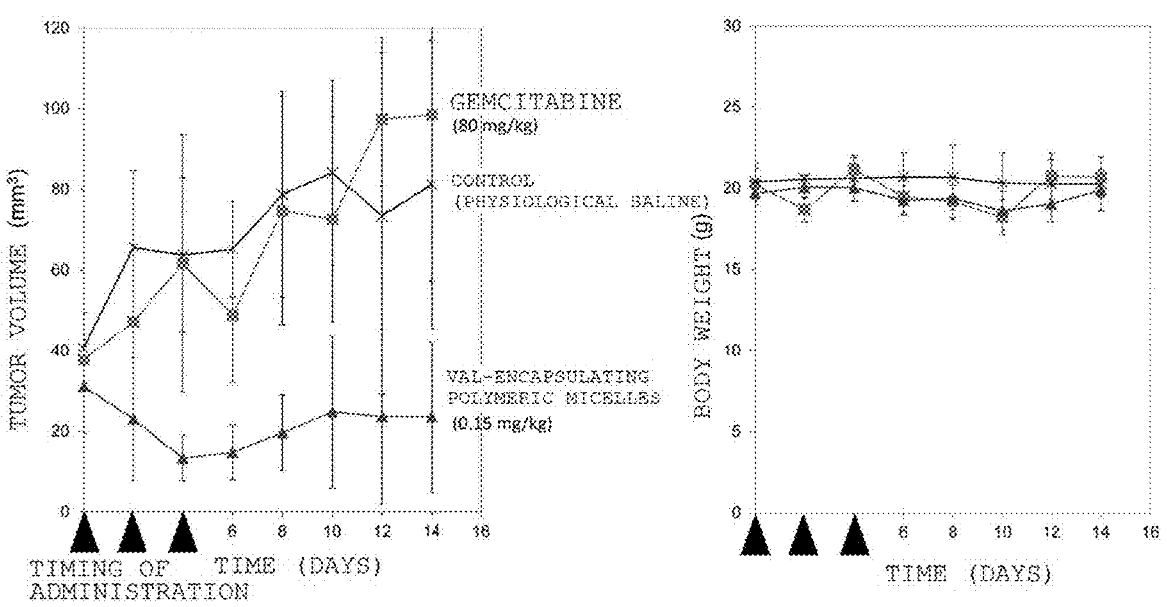
FIG. 8 includes graphs showing the results of evaluation of the antitumor effect of valinomycin-encapsulating polymeric micelles.

As shown in FIG. 8, in the Val-encapsulating polymeric micelle solution administration group, an increase in size of the tumor was remarkably suppressed as compared to a control group (physiological saline administration group) and the gemcitabine solution administration group, but no significant change was found in body weight. All the mice of the valinomycin solution administration group died within 24 hours after the initial administration.

[Test Example 17] Preparation of Unit Host-guest Complex (uHGC)

Val was dissolved in DMSO (10 mg/mL), and 2 kDa PEG-CHO (10 equivalents) and dihydralazine (5 equivalents) were added. After a reaction at room temperature for 24 hours, the resultant was dialyzed (MWCO: 1,000) against methanol, followed by drying under reduced pressure to afford a complex (uHGC) of a delivery carrier and Val shown below. The introduction ratio of Val (ratio of the amount of Val carried by the delivery carrier to the amount of Hyd) was calculated to be 63% from $^{1}$H-NMR in deuterated DMSO.

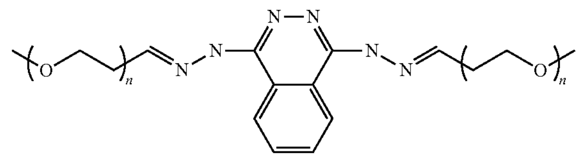

[Test Example 18] Toxicity Test of uHGC against Cultured Cells

Human pancreatic adenocarcinoma cells (B×PC3 cells) were seeded into a 96-well plate (5,000 cells/well), and 24 hours later, uHGC was added. After 48 hours, the cells were washed with PBS, and a medium was added. After that, Cell Counting Kit-8 (CCK-8, 10 μL/well) was added to the medium, and 30 minutes later, UV absorbance at 450 nm was measured. The cell survival rate was calculated from the absorbance between 100% for a group in which only the buffer was added and 0% for a cell-free group. The results are shown in FIG. 9.

Figure 9:
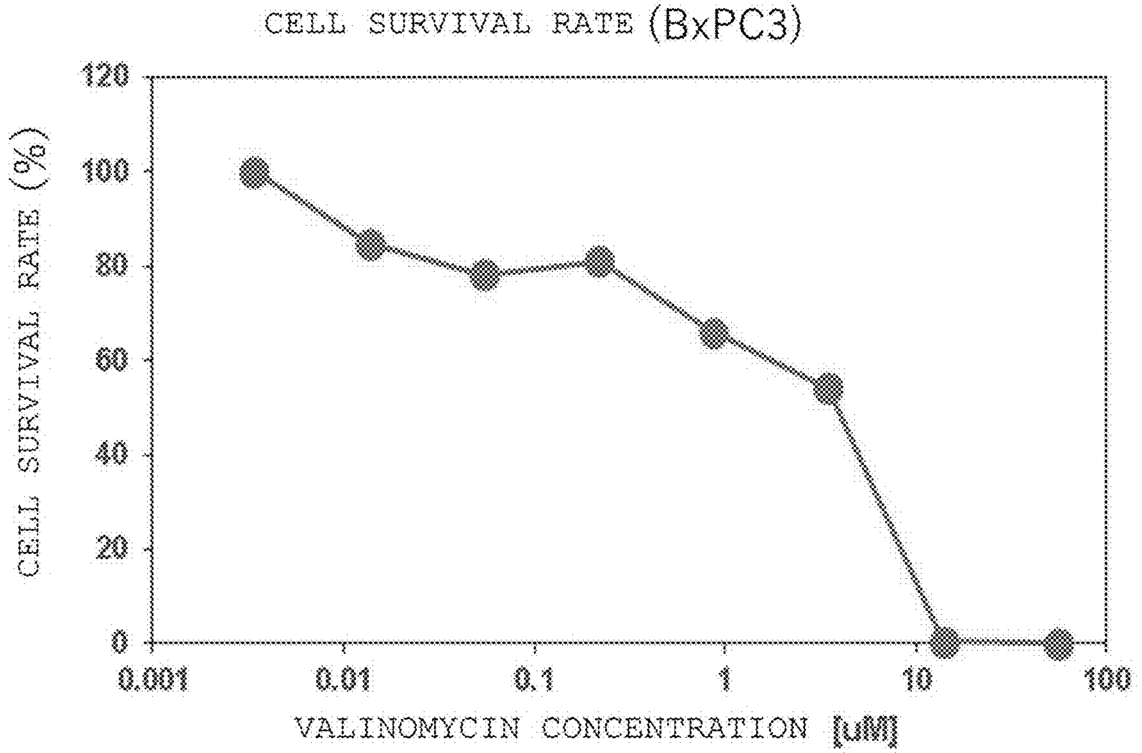
FIG. 9 is a graph showing the results of a toxicity test of uHGC against cultured cells.
Figure 10A:
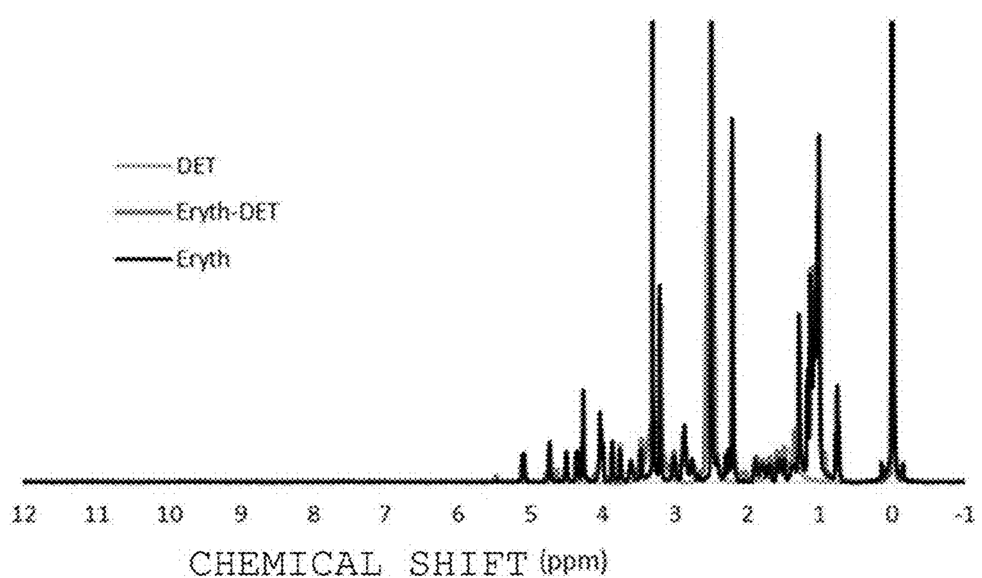
FIG. 10A is a chart showing the results of evaluation of a host-guest interaction between erythromycin and diethylenetriamine by $^{1}$H-NMR.
Figure 10B:
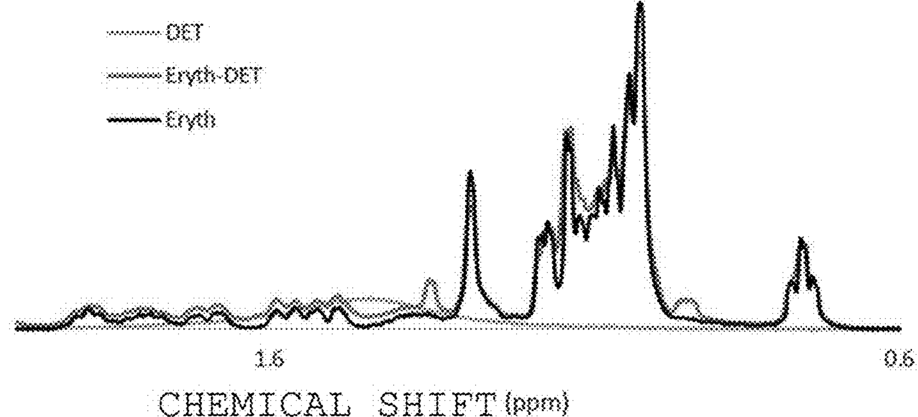
FIG. 10B is a chart showing the results of evaluation of a host-guest interaction between erythromycin and diethylenetriamine by $^{1}$H-NMR.
Figure 10C:
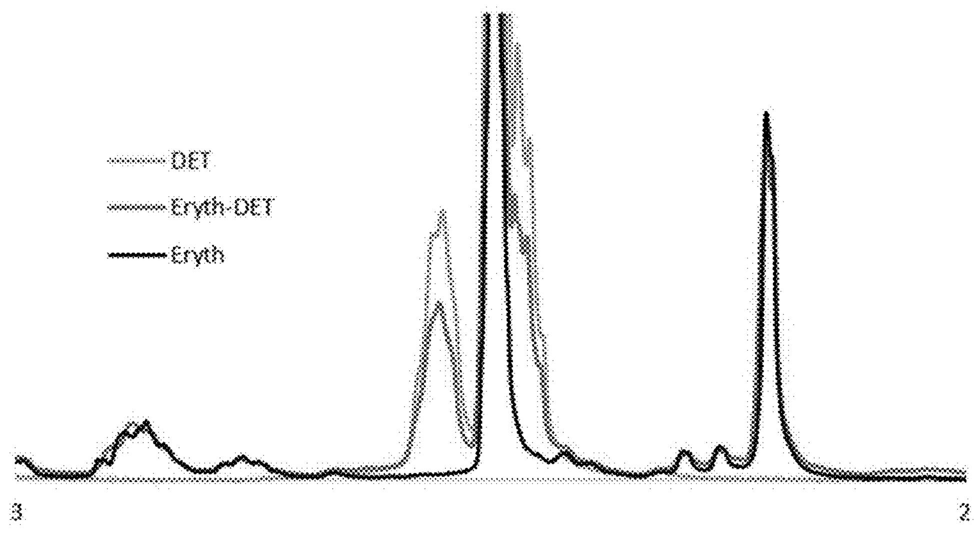
FIG. 10C is a chart showing the results of evaluation of a host-guest interaction between erythromycin and diethylenetriamine by $^{1}$H-NMR.
Figure 10D:
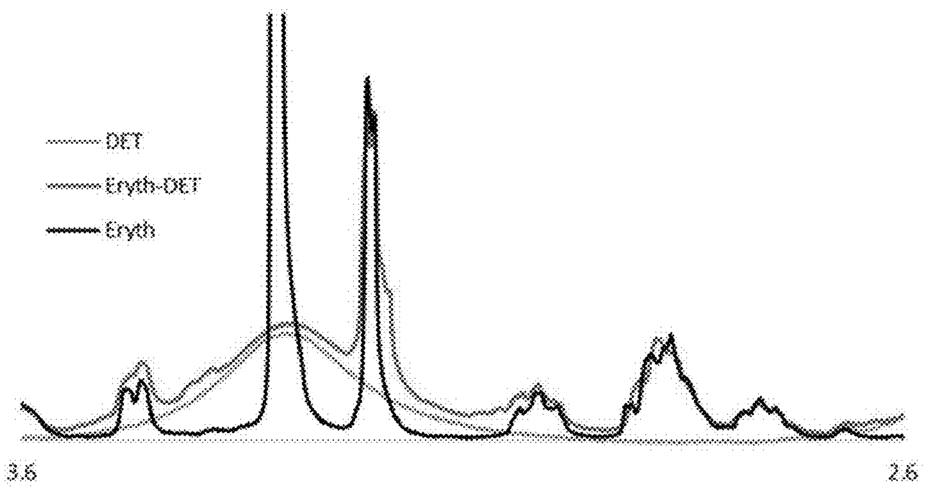
FIG. 10D is a chart showing the results of evaluation of a host-guest interaction between erythromycin and diethylenetriamine by $^{1}$H-NMR.
Figure 10E:
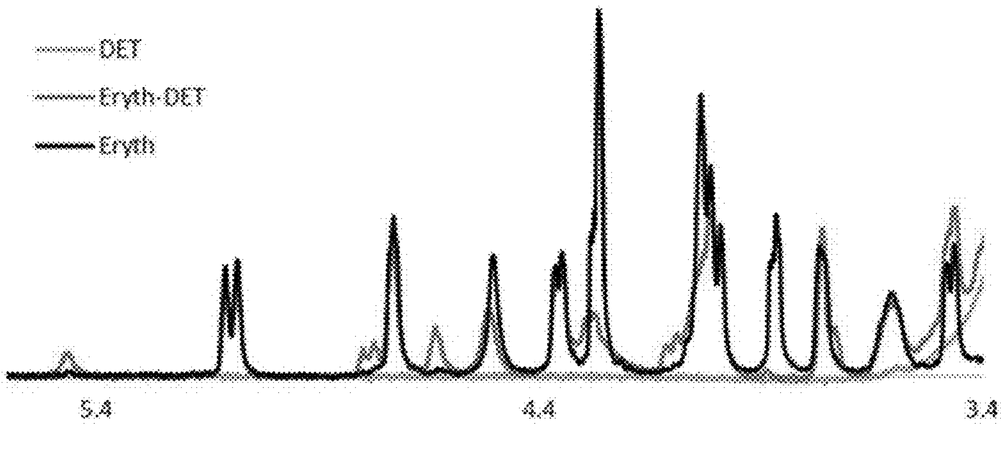
FIG. 10E is a chart showing the results of evaluation of a host-guest interaction between erythromycin and diethylenetriamine by $^{1}$H-NMR.
Figure 11A:
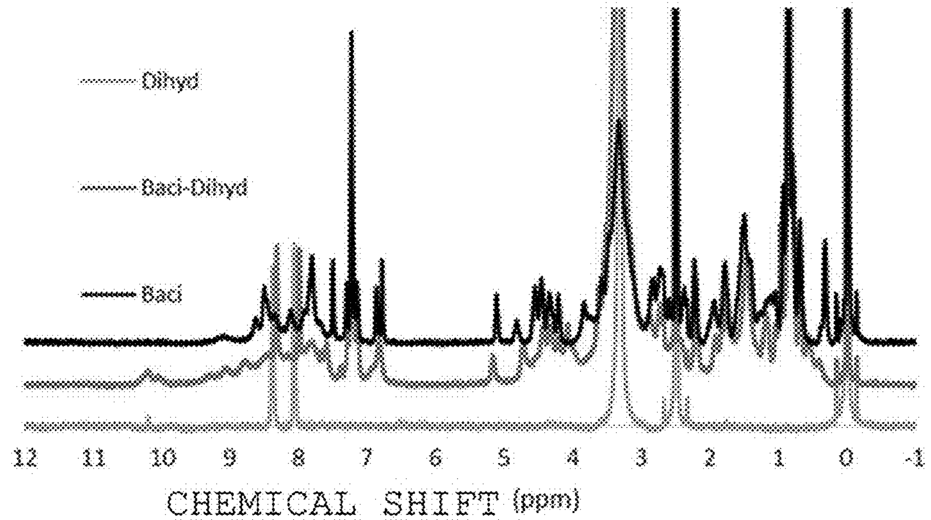
FIG. 11A is a chart showing the results of evaluation of a host-guest interaction between bacitracin and dihydralazine by $^{1}$H-NMR.
Figure 11B:
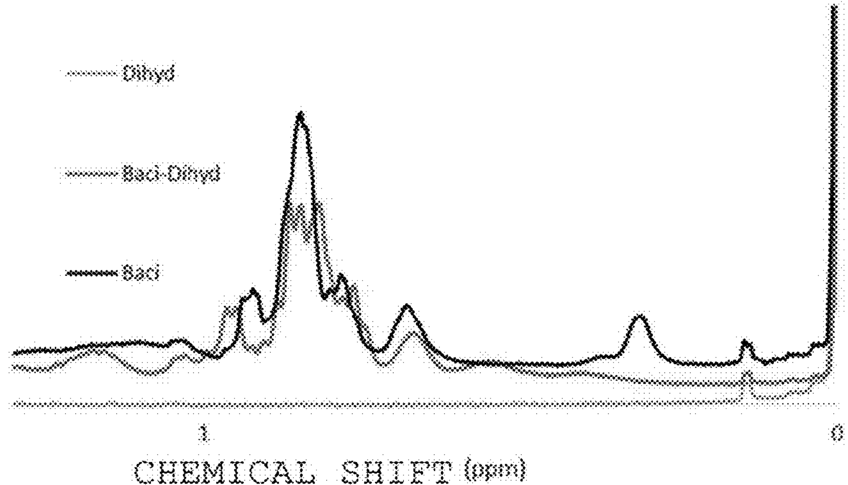
FIG. 11B is a chart showing the results of evaluation of a host-guest interaction between bacitracin and dihydralazine by $^{1}$H-NMR.
Figure 11C:
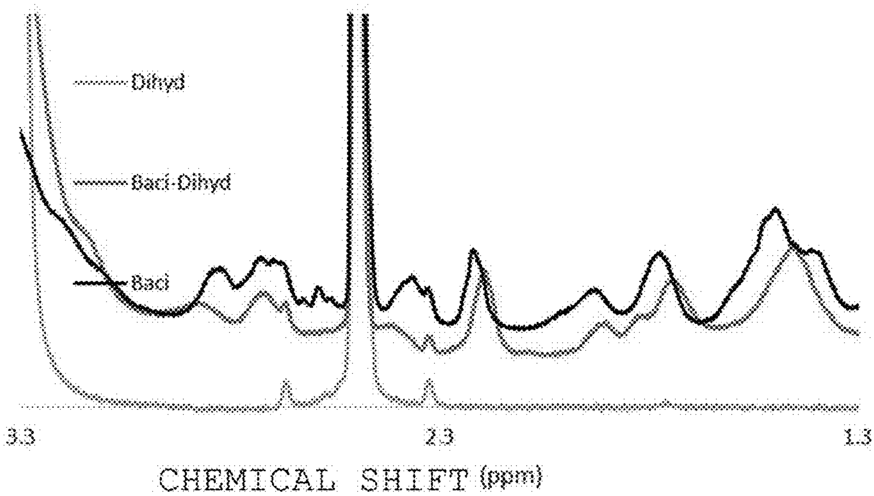
FIG. 11C is a chart showing the results of evaluation of a host-guest interaction between bacitracin and dihydralazine by $^{1}$H-NMR.
Figure 11D:
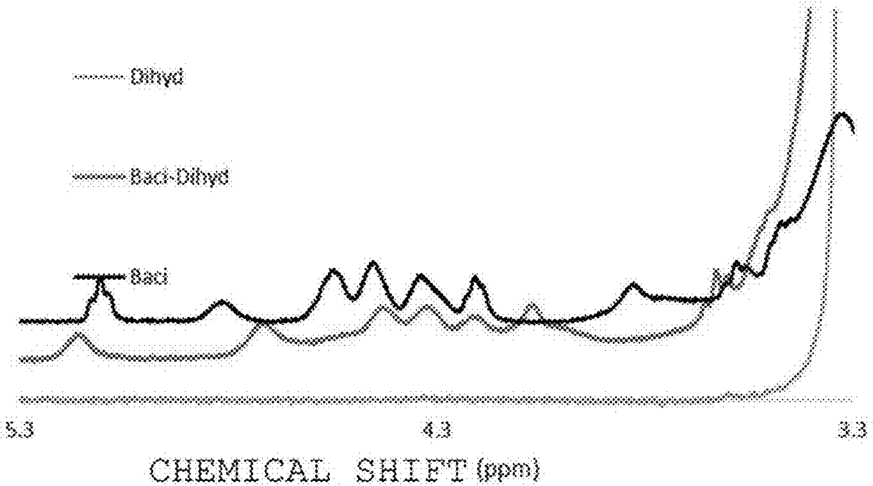
FIG. 11D is a chart showing the results of evaluation of a host-guest interaction between bacitracin and dihydralazine by $^{1}$H-NMR.
Figure 11E:
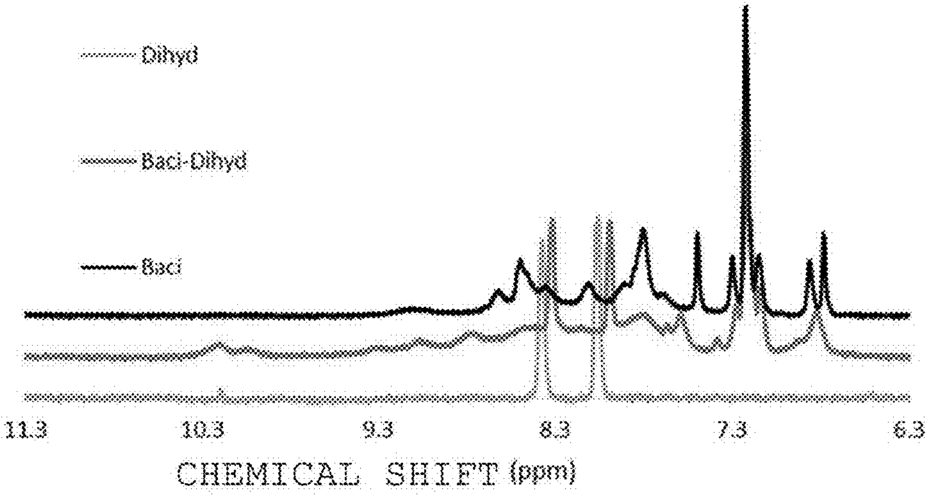
FIG. 11E is a chart showing the results of evaluation of a host-guest interaction between bacitracin and dihydralazine by $^{1}$H-NMR.
Figure 12A:
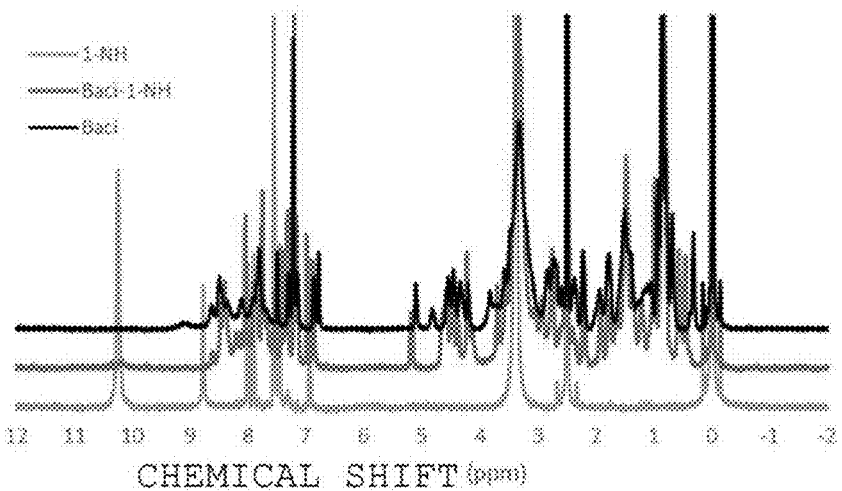
FIG. 12A is a chart showing the results of evaluation of a host-guest interaction between bacitracin and 1-naphthylhydralazine by $^{1}$H-NMR.
Figure 12B:
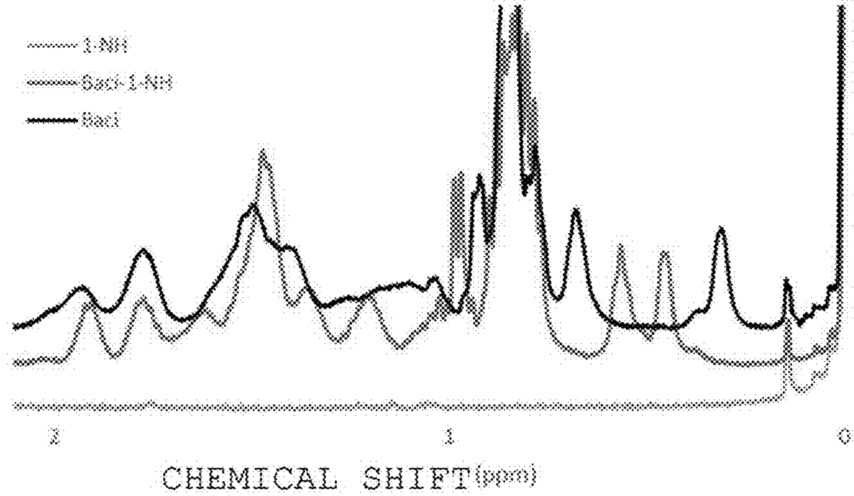
FIG. 12B is a chart showing the results of evaluation of a host-guest interaction between bacitracin and 1-naphthylhydralazine by $^{1}$H-NMR.
Figure 12C:
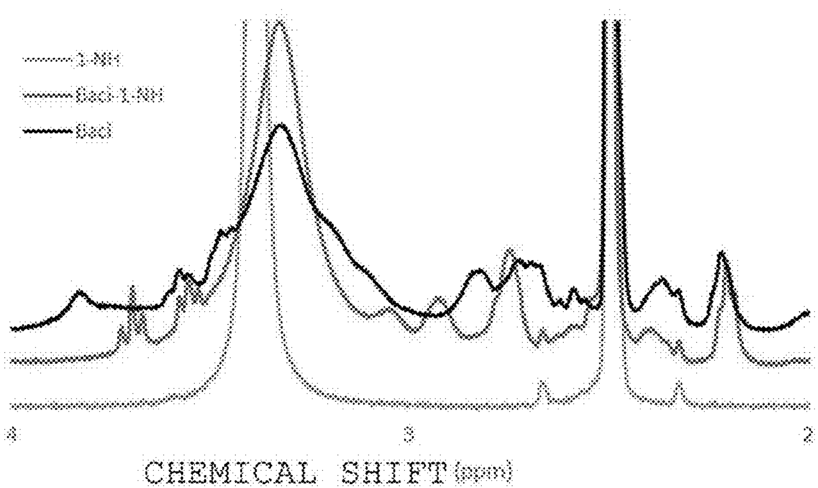
FIG. 12C is a chart showing the results of evaluation of a host-guest interaction between bacitracin and 1-naphthylhydralazine by $^{1}$H-NMR.
Figure 12D:
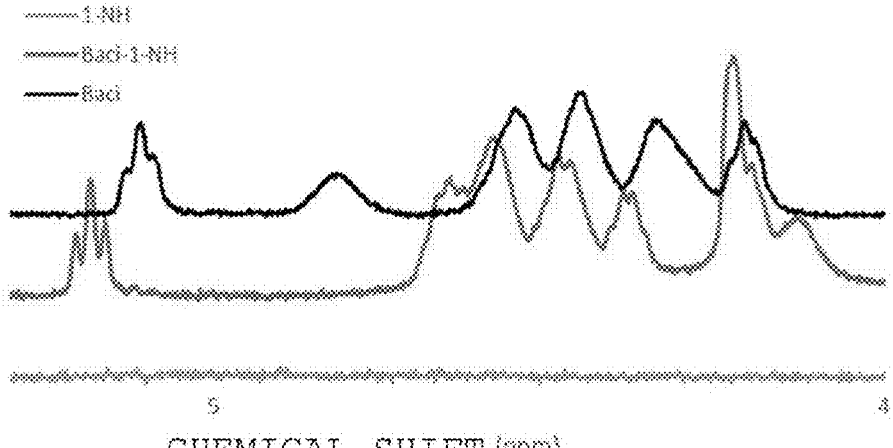
FIG. 12D is a chart showing the results of evaluation of a host-guest interaction between bacitracin and 1-naphthylhydralazine by $^{1}$H-NMR.
Figure 12E:
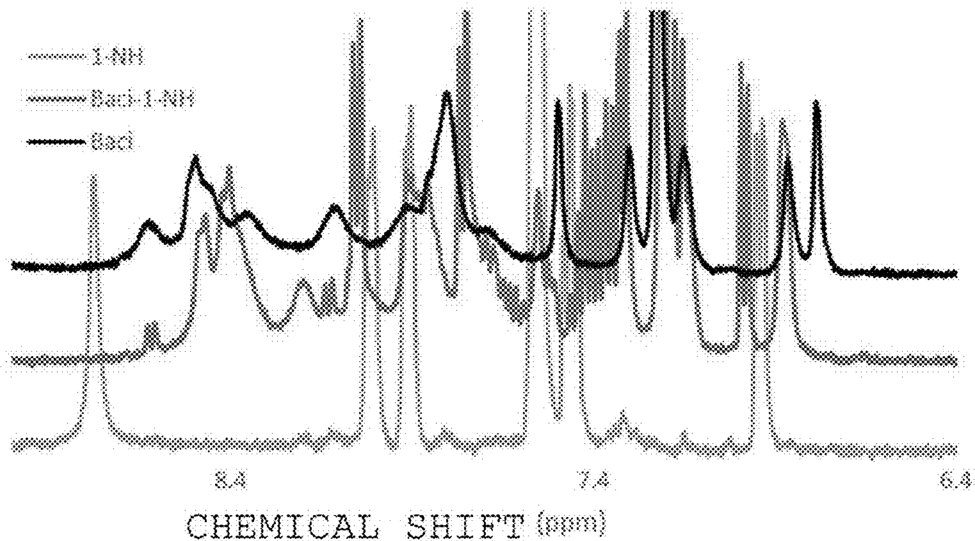
FIG. 12E is a chart showing the results of evaluation of a host-guest interaction between bacitracin and 1-naphthylhydralazine by $^{1}$H-NMR.
Figure 13A:
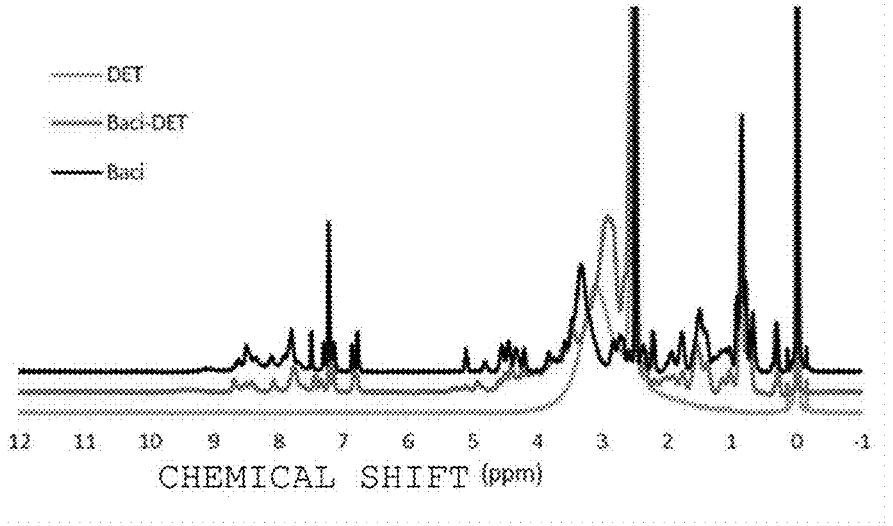
FIG. 13A is a chart showing the results of evaluation of a host-guest interaction between bacitracin and diethylenetriamine by $^{1}$H-NMR.
Figure 13B:
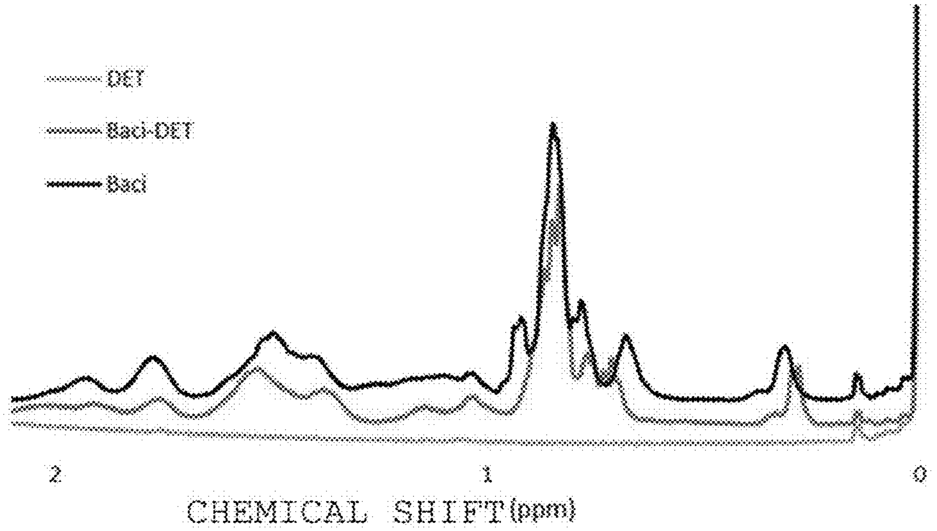
FIG. 13B is a chart showing the results of evaluation of a host-guest interaction between bacitracin and diethylenetriamine by $^{1}$H-NMR.
Figure 13C:
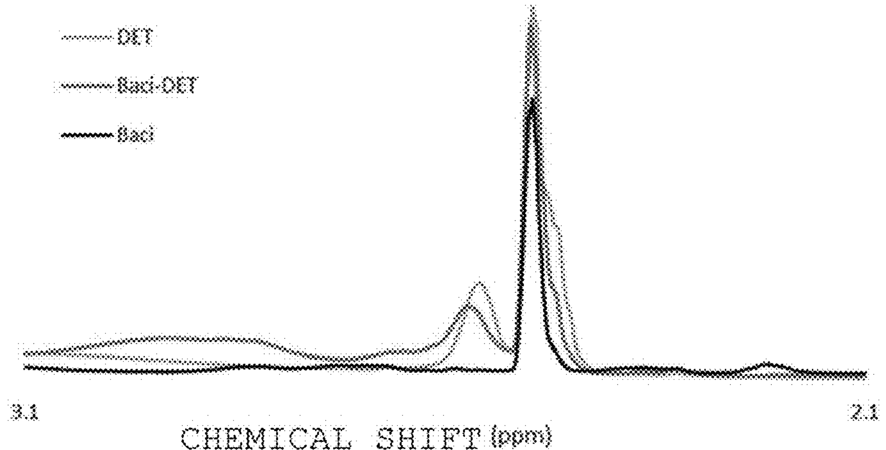
FIG. 13C is a chart showing the results of evaluation of a host-guest interaction between bacitracin and diethylenetriamine by $^{1}$H-NMR.
Figure 13D:
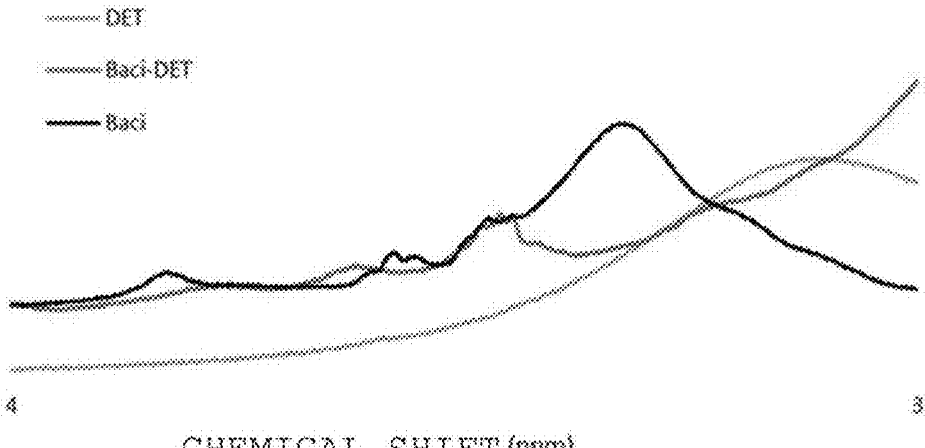
FIG. 13D is a chart showing the results of evaluation of a host-guest interaction between bacitracin and diethylenetriamine by $^{1}$H-NMR.
Figure 13E:
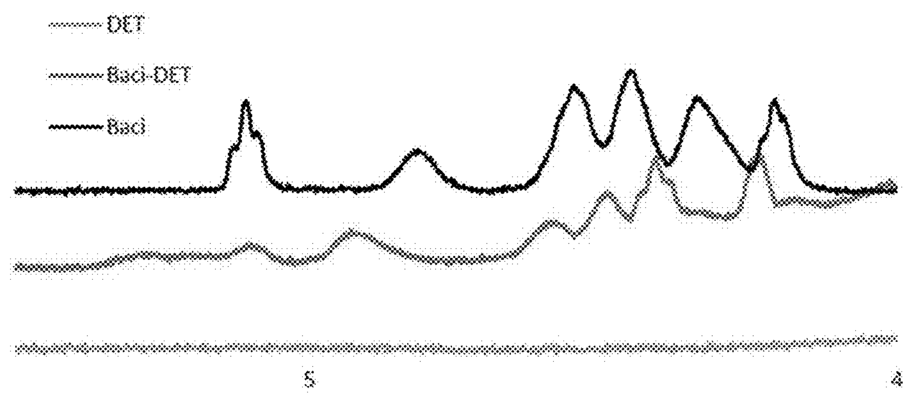
FIG. 13E is a chart showing the results of evaluation of a host-guest interaction between bacitracin and diethylenetriamine by $^{1}$H-NMR.
Figure 13F:
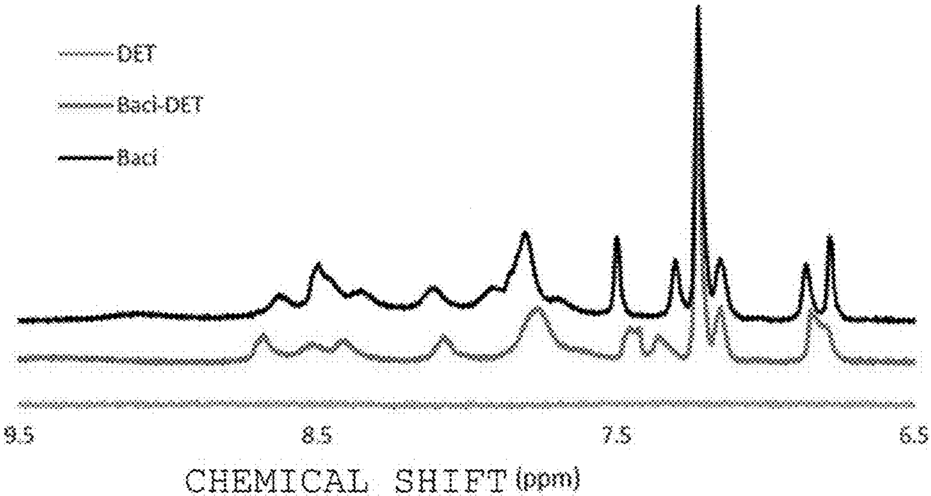
FIG. 13F is a chart showing the results of evaluation of a host-guest interaction between bacitracin and diethylenetriamine by $^{1}$H-NMR.
Figure 14A:
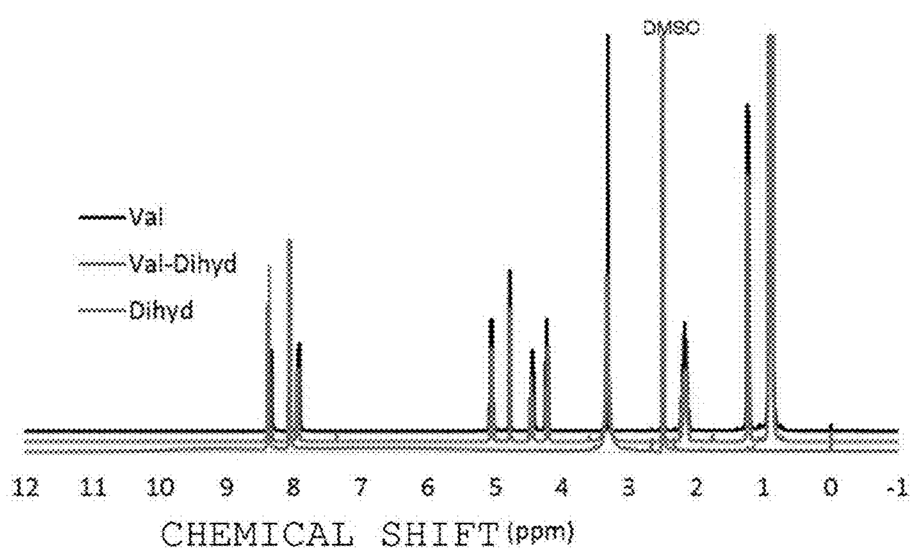
FIG. 14A is a chart showing the results of evaluation of a host-guest interaction between valinomycin and dihydralazine by $^{1}$H-NMR.
Figure 14B:
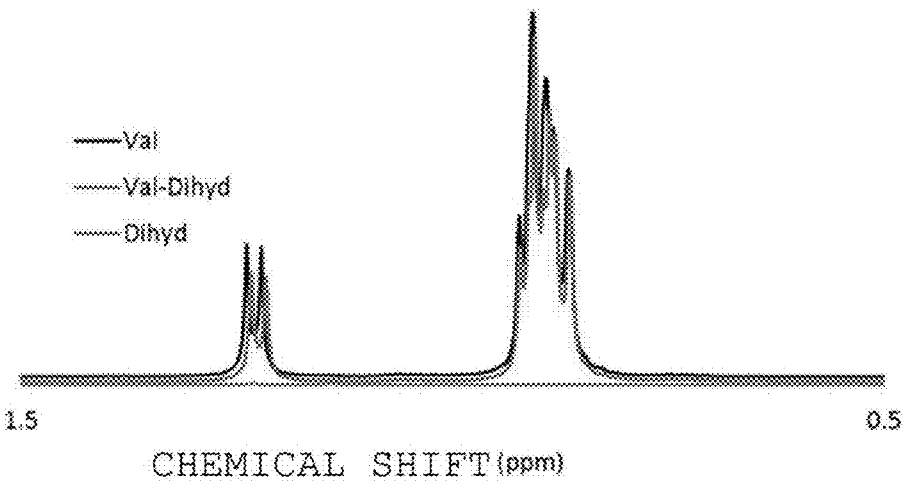
FIG. 14B is a chart showing the results of evaluation of a host-guest interaction between valinomycin and dihydralazine by $^{1}$H-NMR.
Figure 14C:
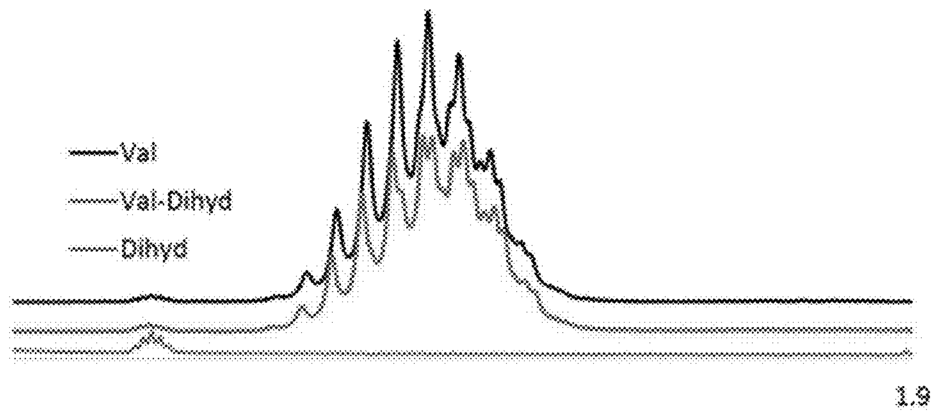
FIG. 14C is a chart showing the results of evaluation of a host-guest interaction between valinomycin and dihydralazine by $^{1}$H-NMR.
Figure 14D:
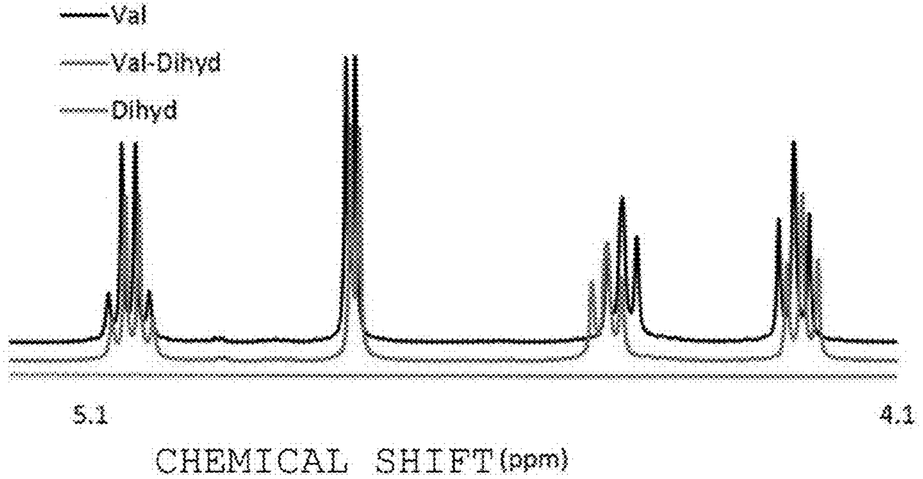
FIG. 14D is a chart showing the results of evaluation of a host-guest interaction between valinomycin and dihydralazine by $^{1}$H-NMR.
Figure 14E:
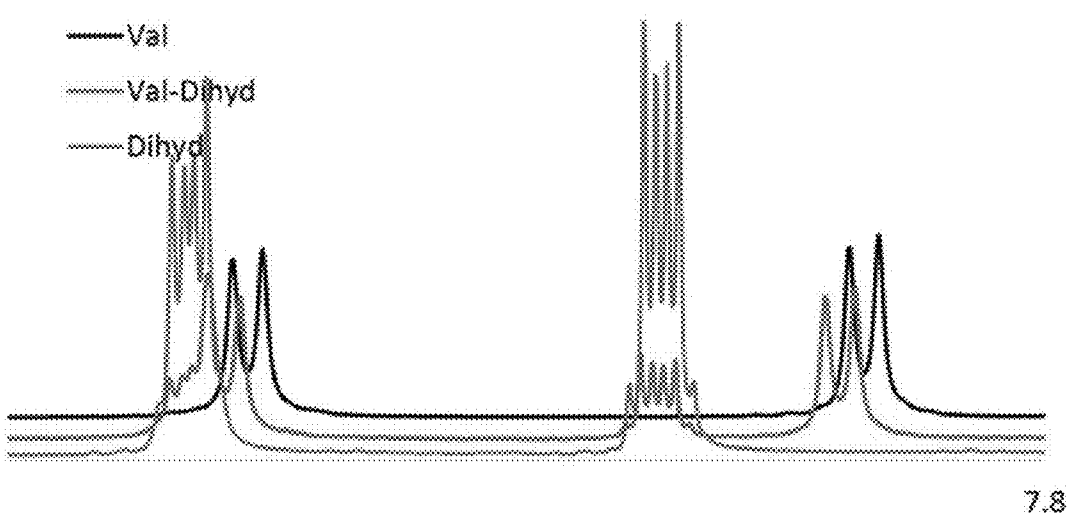
FIG. 14E is a chart showing the results of evaluation a host-guest interaction between valinomycin and dihydralazine by $^{1}$H-NMR.

As shown in FIG. 9, the uHGC addition group shows a cell survival rate of about 70% at a Val concentration of 1 μM, revealing that the toxicity of Val can be suppressed by forming a complex. Meanwhile, through addition of a high concentration of uHGC, a reduction in cell survival rate was observed, suggesting the induction of cell death by the release of the encapsulated valinomycin.

Figure 15:
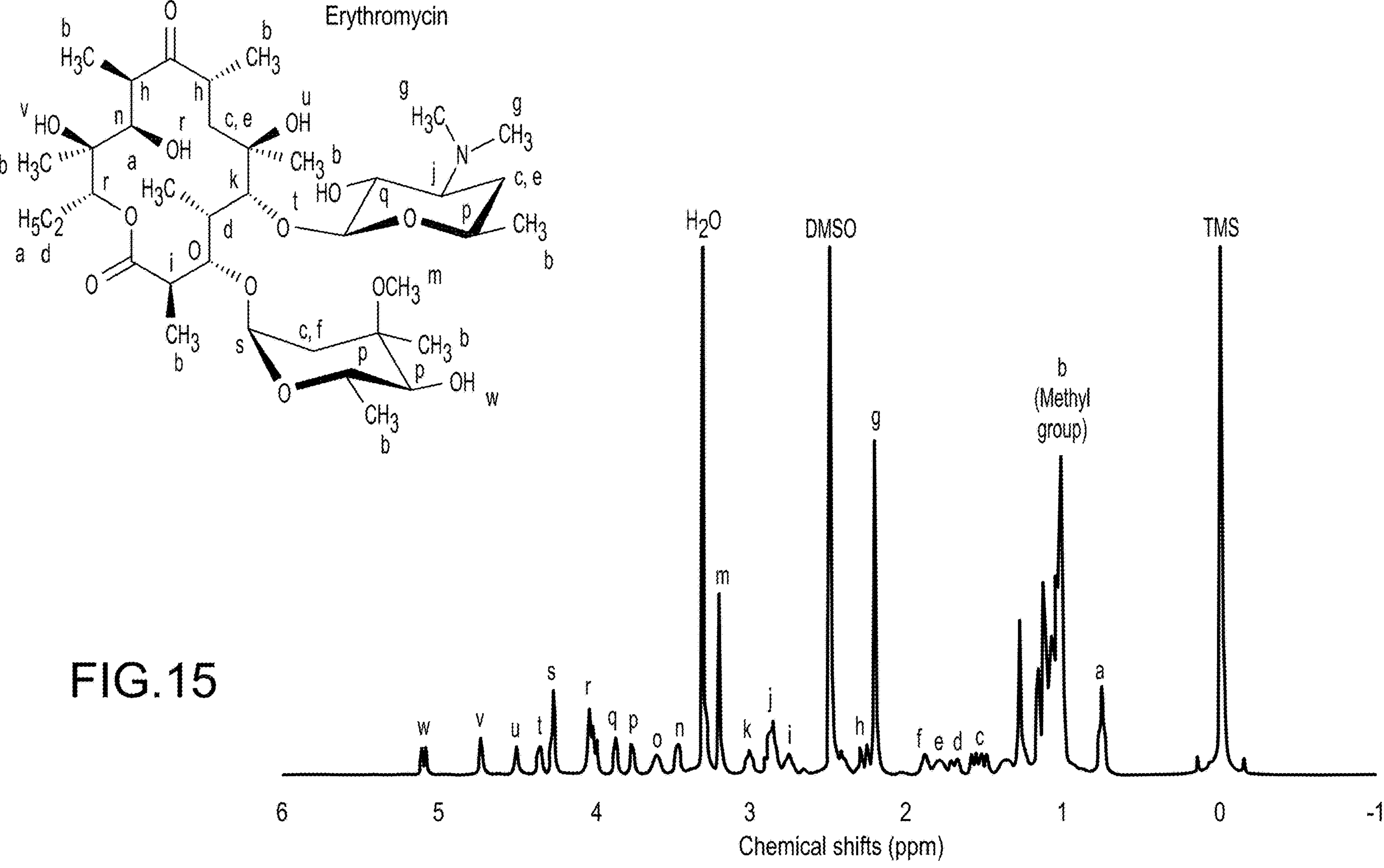
FIG. 15 shows the chemical structure and 1H-NMR measurement results of erythromycin.

[Test Example 19] Investigation 1 of Combination that causes Host-guest Interaction Erythromycin was selected as the cyclic compound. The chemical structure and $^{1}$H-NMR measurement results of erythromycin are shown in FIG. 15.

Figure 16:
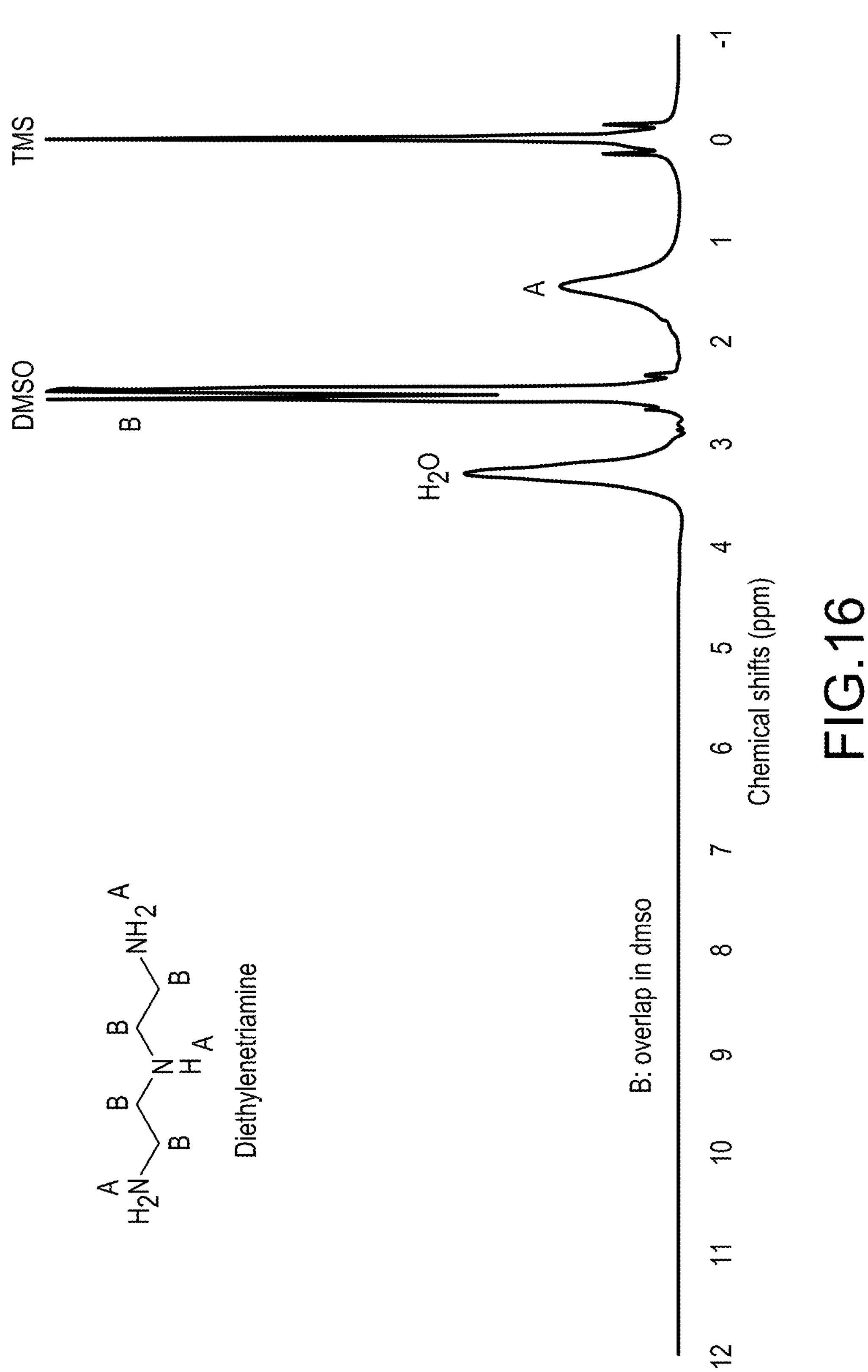
FIG. 16 shows the chemical structure and 1H-NMR measurement results of diethylenetriamine.

The diameter of the ring of erythromycin is 3 Å, and hence a search was made for a guest molecule (shaft portion) candidate capable of causing a host-guest interaction with erythromycin under the criteria of having a molecular diameter of less than 3 Å and having a donor atom having a lone pair, such as a nitrogen atom, in the molecule; as a result, diethylenetriamine (DET) was selected. The chemical structure and $^{1}$H-NMR measurement results of DET are shown in FIG. 16.

Then, an interaction between erythromycin and DET was evaluated as described below. Erythromycin (10 mg/mL) and DET (1.41 mg/mL) were mixed with each other in deuterated DMSO, chemical shifts were measured by $^{1}$H-NMR, and each peak was attributed. As a control, the chemical shifts of each of erythromycin (10 mg/mL) alone and DET (1.41 mg/mL) alone were also measured, and each peak was attributed. The results are shown in FIG. 10A to FIG. 10E.

As shown in FIG. 10A to FIG. 10E, in the case of coexisting with DET, changes occur in chemical shifts in the ring of erythromycin, revealing that DET intermolecularly interacts with the ring structure of erythromycin.

Figure 17:
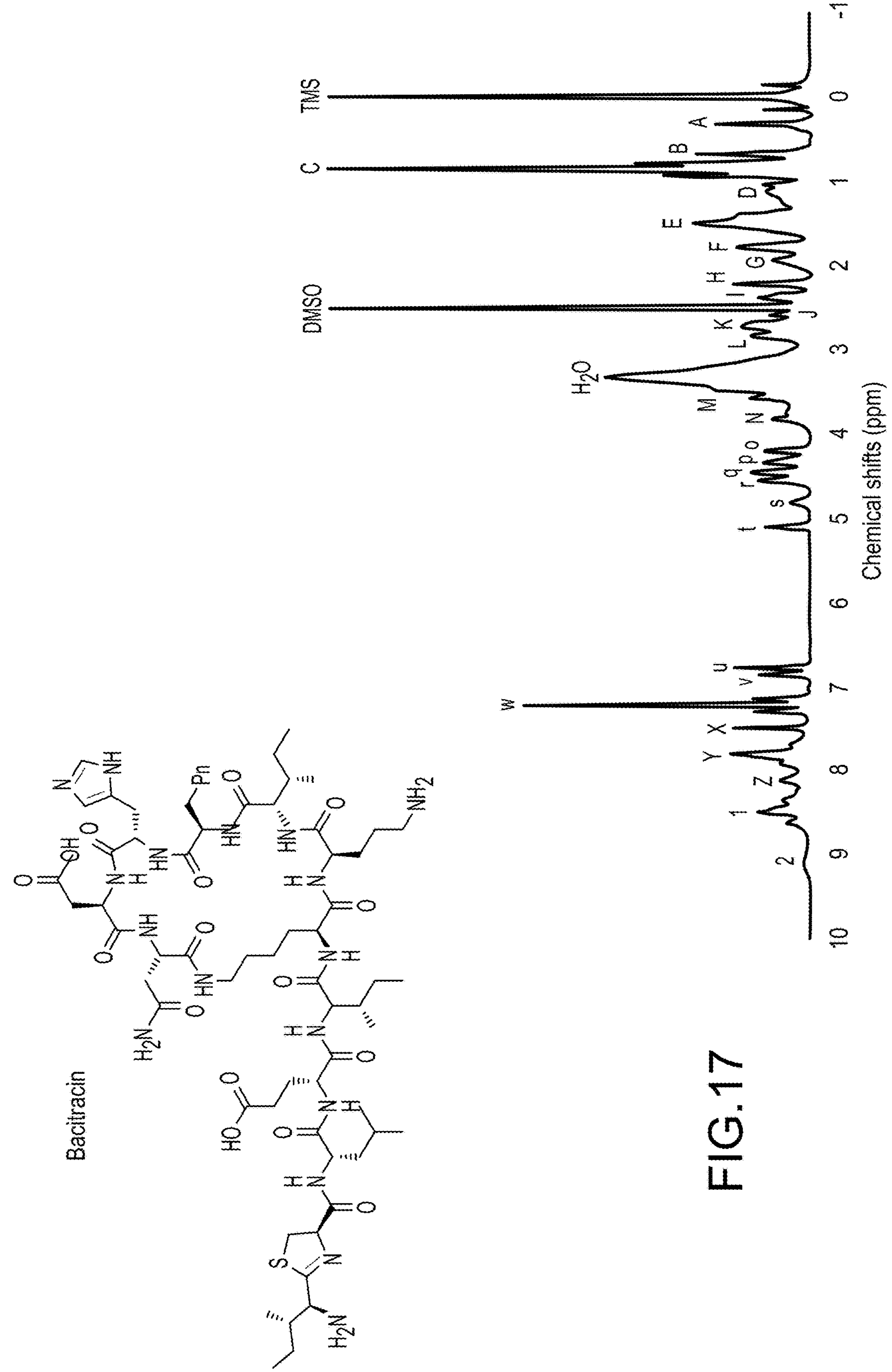
FIG. 17 shows the chemical structure and 1H-NMR measurement results of bacitracin.

[Test Example 20] Investigation 2 of Combination that causes Host-guest Interaction Bacitracin was selected as the cyclic compound. The chemical structure and $^{1}$H-NMR measurement results of bacitracin are shown in FIG. 17.

Figure 18:
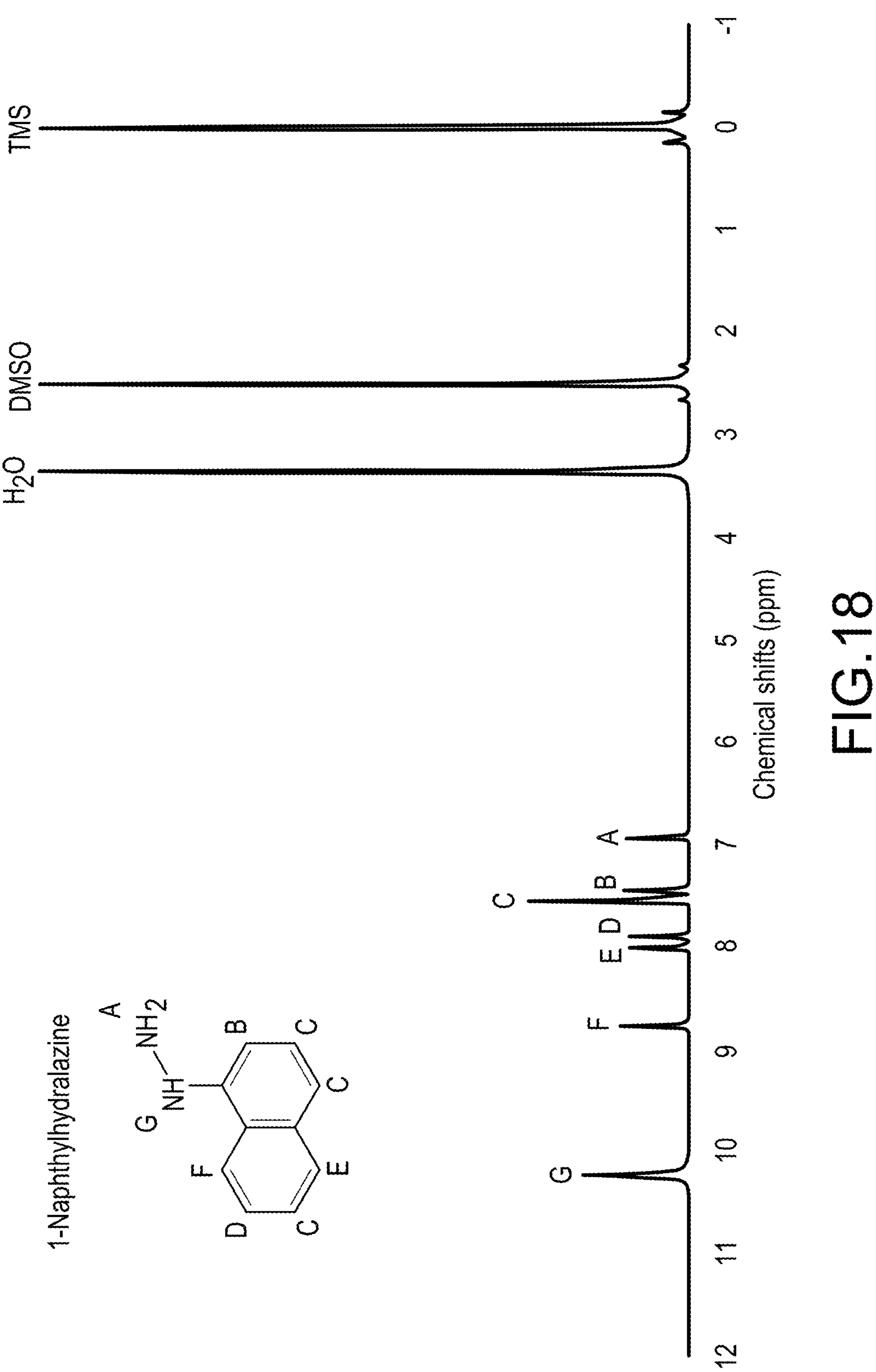
FIG. 18 shows the chemical structure and 1H-NMR measurement results of 1-naphthylhydralazine.
Figure 19:
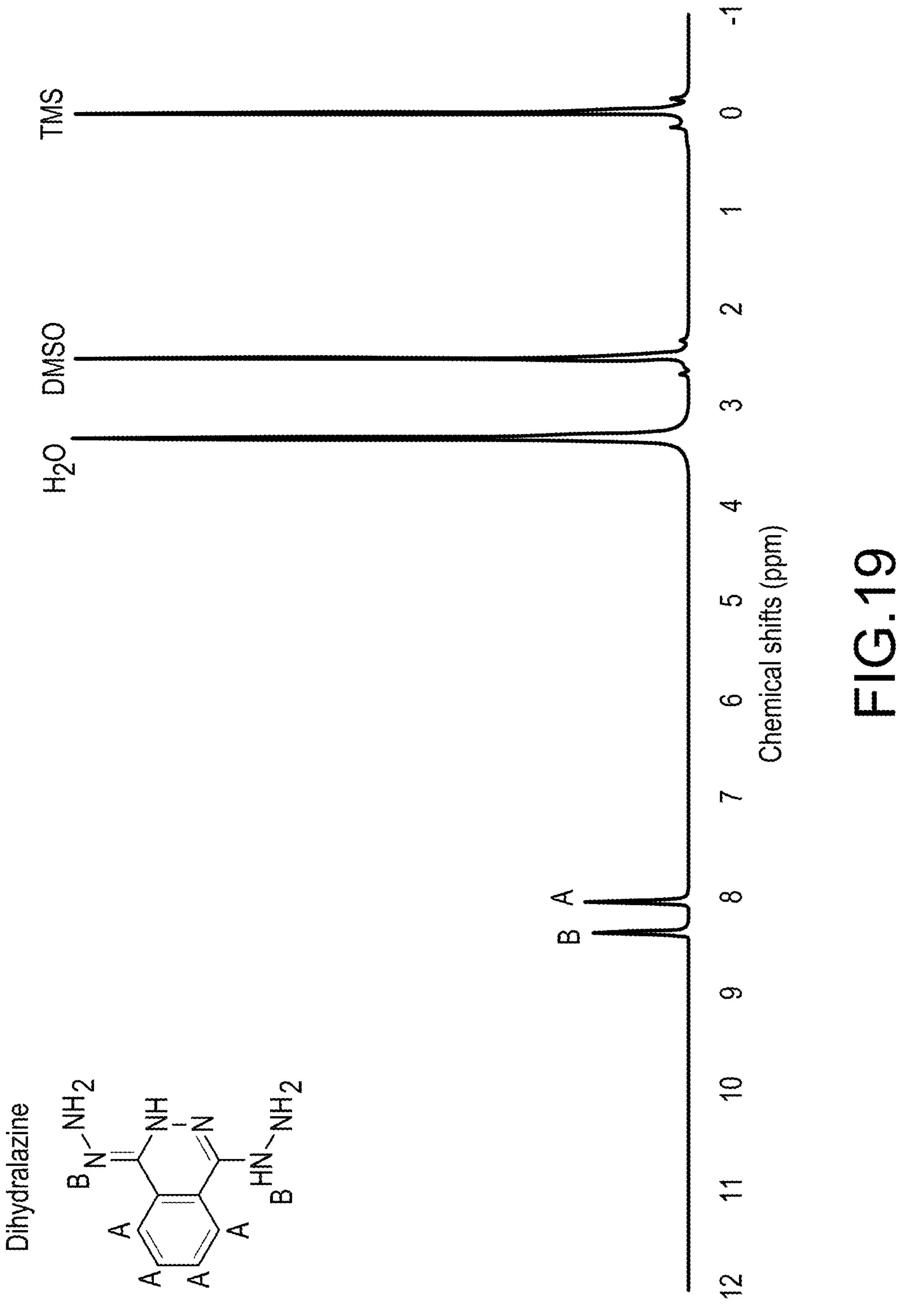
FIG. 19 shows the chemical structure and 1H-NMR measurement results of dihydralazine.

The diameter of the ring of bacitracin is 8 Å, and hence a search was made for a guest molecule (shaft portion) candidate capable of causing a host-guest interaction with bacitracin under the criteria of having a molecular diameter of less than 8 Å and having a donor atom having a lone pair, such as a nitrogen atom, in the molecule. As a result, dihydralazine, 1-naphthylhydralazine, and DET were selected. The chemical structure and $^{1}$H-NMR measurement results of 1-naphthylhydralazine are shown in FIG. 18 and the chemical structure and 1H-NMR measurement results of dihydralazine are shown in FIG.19.

Then, in the same manner as in Test Example 19, an interaction between bacitracin and dihydralazine, 1-naphthylhydralazine, or DET was evaluated on the basis of changes in chemical shifts in $^{1}$H-NMR measurement. The results are shown in FIG. 11A to FIG. 11E, FIG. 12A to FIG. 12E, and FIG. 13A to FIG. 13F, respectively.

As shown in FIG. 11A to FIG. 11E, FIG. 12A to FIG. 12E, and FIG. 13A to FIG. 13F, in the case of coexisting with dihydralazine, 1-naphthylhydralazine, or DET, changes occur in chemical shifts in the ring of bacitracin, revealing that dihydralazine, 1-naphthylhydralazine, or DET intermolecularly interacts with the ring structure of bacitracin.

[Test Example 21] Investigation of Host-guest Interaction between Val and Dihydralazine Val (10 mg/mL) and dihydralazine (2.6 mg/mL) were mixed with each other in deuterated DMSO, chemical shifts were measured by $^{1}$H-NMR, and each peak was attributed. As a control, the chemical shifts of each of Val (10 mg/mL) alone and dihydralazine (2.6 mg/mL) alone were also measured, and each peak was attributed. The results are shown in FIG. 14A to FIG. 14E.

As shown in FIG. 14A to FIG. 14E, in the case of coexisting with dihydralazine, as in the case of coexisting with hydralazine, changes occur in peaks of hydrogen of Val, revealing that an intermolecular interaction occurs between Val and dihydralazine.

The present invention can be suitably used in, for example, the field of DDSs.

The invention claimed is:

1. A complex, comprising:

a cyclic compound; and a delivery carrier having a shaft portion, which is enclosed by the cyclic compound and forms an inclusion complex of the cyclic compound with the delivery carrier, and cap portions, which are arranged at both ends of the shaft portion and prevent the cyclic compound from being detached from the shaft portion;

wherein the shaft portion comprises a residue formed from hydralazine, dihydralazine, 1-naphthylhydralazine, or diethylenetriamine.

2. The complex according to claim 1, wherein the cap portions each contain a hydrophilic polymer.

3. The complex according to claim 1, wherein an in vivo cleavable bond is present between the shaft portion and each of the cap portions.

4. The complex according to claim 1, wherein the cyclic compound is selected from the group consisting of valinomycin, bacitracin, and erythromycin.

5. The complex according to claim 3, wherein the cap portions each contain a hydrophilic polymer.

6. The complex according to claim 5, wherein the cyclic compound is selected from the group consisting of valinomycin, bacitracin, and erythromycin.

7. The complex according to claim 2, wherein the cyclic compound is selected from the group consisting of valinomycin, bacitracin, and erythromycin.

8. The complex according to claim 3, wherein the cyclic compound is selected from the group consisting of valinomycin, bacitracin, and erythromycin.

* * * * *